US009353437B2

(12) United States Patent
Han

(10) Patent No.: US 9,353,437 B2
(45) Date of Patent: May 31, 2016

(54) DIAZADIENE-BASED METAL COMPOUND, METHOD FOR PREPARING SAME AND METHOD FOR FORMING A THIN FILM USING SAME

(75) Inventor: Won Seok Han, Anseong-si (KR)

(73) Assignee: UP Chemical Co., Ltd., Pyeongtaek-si (KR)

( * ) Notice: Subject to any disclaimer, the term of this patent is extended or adjusted under 35 U.S.C. 154(b) by 129 days.

(21) Appl. No.: 13/885,740

(22) PCT Filed: Nov. 17, 2011

(86) PCT No.: PCT/KR2011/008791
§ 371 (c)(1),
(2), (4) Date: May 16, 2013

(87) PCT Pub. No.: WO2012/067439
PCT Pub. Date: May 24, 2012

(65) Prior Publication Data
US 2013/0251903 A1 Sep. 26, 2013

(30) Foreign Application Priority Data
Nov. 17, 2010 (KR) .................. 10-2010-0114515

(51) Int. Cl.
C23C 16/18 (2006.01)
C07F 13/00 (2006.01)
C07F 15/04 (2006.01)
C07F 15/06 (2006.01)
C23C 16/06 (2006.01)
C23C 16/40 (2006.01)

(52) U.S. Cl.
CPC ............... C23C 16/18 (2013.01); C07F 13/005 (2013.01); C07F 15/045 (2013.01); C07F 15/065 (2013.01); C23C 16/06 (2013.01); C23C 16/406 (2013.01)

(58) Field of Classification Search
None
See application file for complete search history.

(56) References Cited

U.S. PATENT DOCUMENTS

| 5,874,131 | A | 2/1999 | Vaartstra et al. |
| 2007/0160761 | A1 | 7/2007 | Reuter et al. |
| 2013/0164456 | A1* | 6/2013 | Winter .................... C23C 16/34 427/535 |

FOREIGN PATENT DOCUMENTS

| JP | 2002-542397 A | 12/2002 |
| KR | 10-2010-0061183 A | 6/2010 |
| WO | WO 2010/079979 A2 | 7/2010 |

OTHER PUBLICATIONS

Walther—1992—Inst Anorg Anal Chem V125 No. 7 p. 1529-36.*
(Continued)

Primary Examiner — Joseph Miller, Jr.
(74) Attorney, Agent, or Firm — Greer Burns & Crain Ltd.

(57) ABSTRACT

The present invention relates to a diazadiene (DAD)-based metal compound, to a method for preparing the same and to a method for forming a thin film using the same. The diazadiene (DAD)-based metal compound of the present invention is provided in a gaseous state to be formed into a metal thin film or a metal oxide thin film by chemical vapor deposition or atomic layer deposition. Particularly, the diazadiene-based organic metal compound of the present invention has advantages in that it may be formed into a metal thin film or a metal oxide thin film and it can be prepared in a relatively inexpensive way without using highly toxic ligands.

10 Claims, 15 Drawing Sheets

(56) References Cited

OTHER PUBLICATIONS

Walther—1992—Inst Anorg Anal Chem—English Abstract and related formula.*

Comuzzi, Inorganica Chimica Acta, 2003, V355, p. 57-63.*

Thomas J. Knisley et al., "Volatility and High Thermal Stability in Mid- to Late-First-Row Transition-Metal Diazadienyl Complexes". Organomeiallics, Aug. 25, 2011, vol. 10, p. 5010-5017.

Kirchmann, M. et al. 'Octahedral Coordination Compounds of the Ni, Pd, Pt Triad' Angew, Chem. Int. Ed., Dec. 20, 2007, vol. 47(5), pp. 963-966.

Schaub, T. & Radius, U. 'A Diazabutadiene stabilized Nickel(0) Cyclooctadiene Complex: Synthesis, Characterization and the Reaction with Diphenylacetylene' Z. Anorg. Allg. Chem. Mar. 30, 2006, vol. 632(5), pp. 807-813.

Tromp. D. S. et al. 'Synthesis of new ($\sigma$2-N,N'-diazadiene)($\eta$2-alkene) platinum(0) compounds' Inorganica Chimica Acta, Dec. 8, 2001, vol. 327(1), pp. 90-97.

Baker, R. J. et al. 'An EPR and ENDOR Investigation of a Series of Diazabutadiene-Group 13 Complexes' Chem. Eur. J., May 6, 2005, vol. 11(10), pp. 2972-2982.

International Search Report of PCT/KR2011/008791 dated May 8, 2012.

* cited by examiner

DIAZADIENE-BASED METAL COMPOUND, METHOD FOR PREPARING SAME AND METHOD FOR FORMING A THIN FILM USING SAME

This application is a U.S. National Phase under 35 U.S.C. §371 of International Application No. PCT/KR2011/008791, filed Nov. 17, 2011.

TECHNICAL FIELD

The present disclosure relates to a diazadiene-based metal compound, a preparing method therefor and a method for forming a thin film containing nickel, cobalt or manganese using the same.

BACKGROUND ART

In order to form a metal silicide or a magnetic thin film, a metal thin film of nickel, cobalt or manganese needs to be formed by chemical vapor deposition or atomic layer deposition. A cobalt oxide film or a nickel oxide film may be applied to a sensor or the like. Especially, a method for forming a nickel oxide film by chemical vapor deposition or atomic layer deposition as a memory substance to be used in a resistance random access memory (RRAM) is increasingly attracting attention. A manganese oxide film may be used as a copper diffusion barrier film in a copper wiring.

There is known a method of forming a thin film containing cobalt or nickel by chemical vapor deposition or atomic layer deposition by using a cobalt carbonyl compound or a nickel carbonyl compound. In general, however, carbonyl compounds of cobalt and nickel have a drawback in that they have low thermal stability and high toxicity.

There is also known a method of forming a nickel metal film by chemical deposition by using a tetrakistrifluorophosphine-nickel [$Ni(PF_3)_4$] compound which is a liquid at a room temperature [Y. Ohshita, M. Ishikawa, T. Kada, H. Machida and A. Ogura, *Japanese Journal of Applied Physics,* 44, L315 (2005)]. A $PF_3$ raw material necessary to synthesize the $Ni(PF_3)_4$ compound, however, has high toxicity and is of a high price. Furthermore, $PF_3$ is a compound which is under regulation. Thus, large scale application of $PF_3$ is deemed to be inappropriate.

There is also known a chemical vapor deposition method using cobalt chloride, nickel chloride, a compound obtained as a result of combining cobalt or nickel with a beta-diketonate or beta-ketoiminate ligand. However, since these materials are solid at a room temperature and have low vapor pressure, it may be difficult to apply these materials to the manufacture of a semiconductor device.

There are also reported amidinate compounds of nickel, cobalt, and manganese that may be applicable to atomic layer deposition [B. S. Lim, A. Rahtu, J. S. Park, and R. G. Gordon, *Inorganic Chemistry,* 42, 7951 (2003)]. Since, however, these materials are also solid at a room temperature, it may be disadvantageous to use these materials in the atomic layer deposition or chemical deposition.

DISCLOSURE OF THE INVENTION

Problems to Be Solved by the Invention

In view of the forgoing problems, the present disclosure provides a diazadiene-based metal compound applicable to chemical deposition or atomic layer deposition and a preparing method therefor. Further, the present disclosure also provides a method for forming a thin film by using the diazadiene-based metal compound.

However, the problems sought to be solved by the present disclosure are not limited to the above description and other problems can be clearly understood by those skilled in the art from the following description.

Means for Solving the Problems

In accordance with a first aspect of the present disclosure, there is provided a diazadiene (DAD)-based metal compound represented by any one of the following chemical formulas 1 to 4.

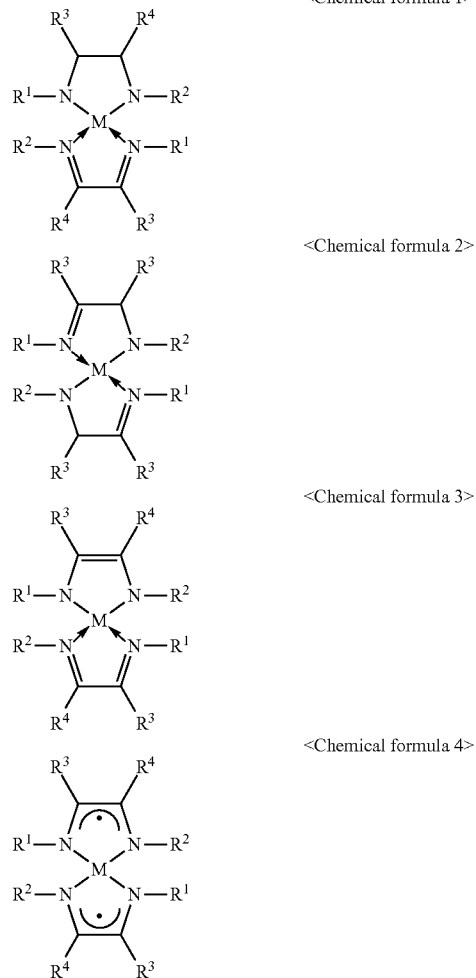

Wherein in the chemical formulas 1 to 4,
M denotes Ni, Co or Mn, and
each of $R^1$ to $R^4$ denotes independently hydrogen, or a linear or branched alkyl group having a carbon number ranging from about 1 to about 6.

In accordance with a second aspect of the present disclosure, there is provided a method for preparing a diazadiene-based metal compound, as indicated by the following reaction formula 1, comprising reacting a diazadiene neutral ligand represented by the following chemical formula 5 with a hydrogen reducing agent to synthesize a diazadiene-induced bivalent negative ion; and reacting the diazadiene neutral ligand represented by the following chemical formula 5 with a bivalent halogen metal compound represented by $MX_2$ and then adding the diazadiene-induced bivalent negative ion thereto to thereby allow a reaction therebetween.

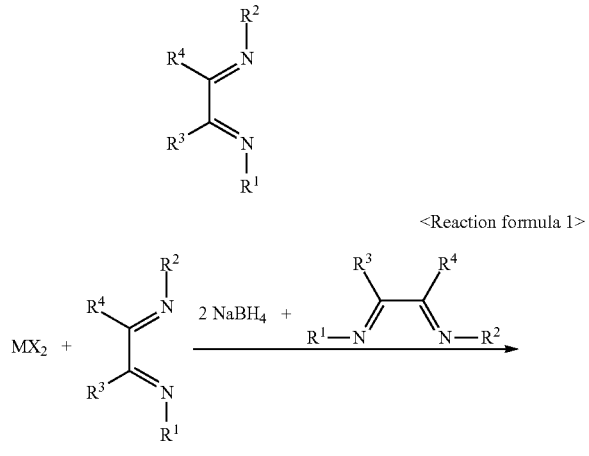

<Chemical formula 5>

<Reaction formula 1>

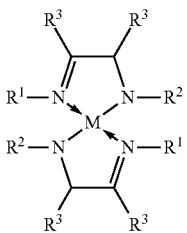

Wherein X denotes Cl, Br or I, M denotes Ni, Co or Mn, and each of $R^1$ to $R^4$ denotes independently hydrogen, or a linear or branched alkyl group having a carbon number ranging from about 1 to about 6.

In accordance with a fourth aspect of the present disclosure, there is provided a method for preparing a diazadiene-based metal compound, as indicated by the following reaction formula 3, comprising reacting a diazadiene neutral ligand represented by the following chemical formula 5 with an alkaline metal M' to synthesize a diazadiene-induced bivalent negative ion; and reacting the diazadiene neutral ligand represented by the following chemical formula 5 with a bivalent halogen metal compound represented by $MX_2$ and then adding the diazadiene-induced bivalent negative ion thereto to thereby allow a reaction therebetween.

Wherein X denotes Cl, Br or I, M denotes Ni, Co or Mn, and each of $R^1$ to $R^4$ denotes independently hydrogen, or a linear or branched alkyl group having a carbon number ranging from about 1 to about 6.

In accordance with a third aspect of the present disclosure, there is provided a method for preparing a diazadiene-based metal compound, as indicated by the following reaction formula 2, comprising reacting a diazadiene neutral ligand represented by the following chemical formula 6 with a hydrogen reducing agent to synthesize a diazadiene-induced monovalent negative ion; and adding a bivalent halogen metal compound represented by $MX_2$ to the diazadiene-induced monovalent negative ion to allow a reaction therebetween.

<Chemical formula 5>

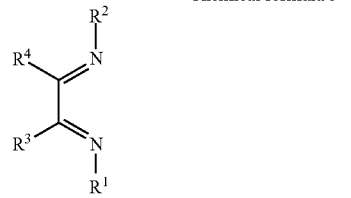

<Reacton formula 3>

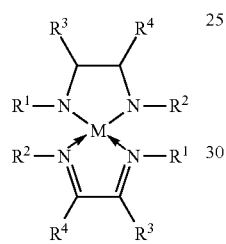

<Chemical formula 6>

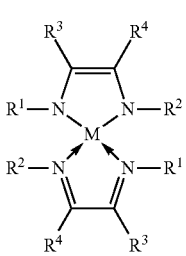

<Reaction formula 2>

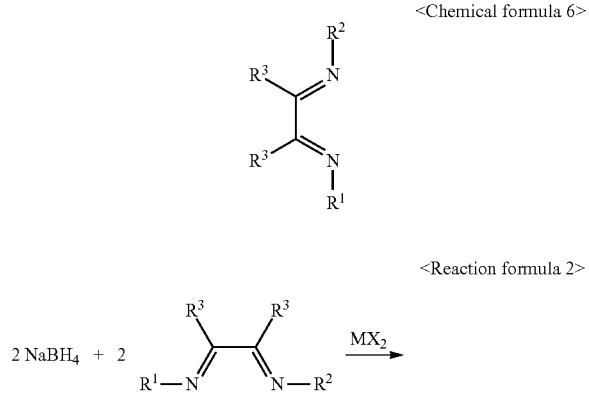

Wherein M' denotes Li, Na or K, X denotes Cl, Br or I, M denotes Ni, Co or Mn, and each of $R^1$ to $R^4$ denotes independently hydrogen, or a linear or branched alkyl group having a carbon number ranging from about 1 to about 6.

In accordance with a fifth aspect of the present disclosure, there is provided a method for preparing a diazadiene-based metal compound, as indicated by the following reaction formula 4, comprising reacting a diazadiene neutral ligand represented by the following chemical formula 5 with a alkaline metal M' to synthesize a diazadiene-induced monovalent negative ion; and adding a bivalent halogen metal compound represented by $MX_2$ to the diazadiene-induced monovalent negative ion to thereby allow a reaction therebetween.

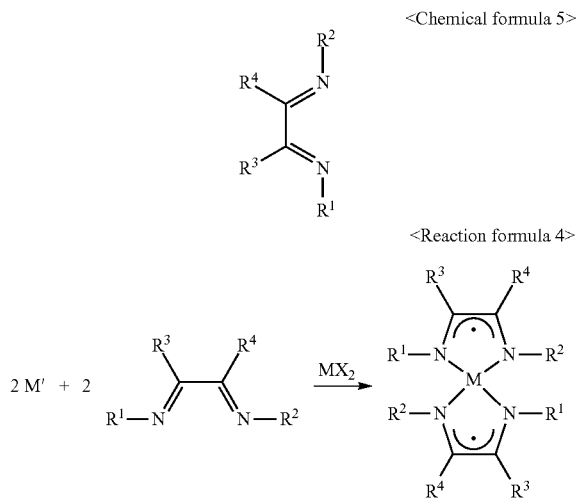

<Chemical formula 5>

<Reaction formula 4>

Wherein M' denotes Li, Na or K, X denotes Cl, Br or I, M denotes Ni, Co or Mn, and each of $R^1$ to $R^4$ denotes independently hydrogen, or a linear or branched alkyl group having a carbon number ranging from about 1 to about 6.

In accordance with a sixth aspect of the present disclosure, there is provided a thin film forming method, comprising depositing a diazadiene-based metal compound in accordance with the first aspect of the present disclosure used as a source material on a substrate by chemical vapor deposition or atomic layer deposition to form a metal thin film containing nickel, cobalt or manganese.

Effect of the Invention

In accordance with the present disclosure, by supplying the diazadiene-based metal compound in a gaseous state, a thin film containing nickel, cobalt or manganese can be formed by chemical deposition or atomic layer deposition. Especially, the diazadiene-based organic metal compound in accordance with the present disclosure has advantages in that it can be used in forming a metal thin film and can be prepared at a low cost without needing to use a ligand having high toxicity.

A nickel or cobalt thin film formed on silicon by using the diazadiene-based nickel or cobalt compound in accordance with the present disclosure may be used for a contact of a semiconductor device or the like after it is heat-treated and a metal silicide is formed thereon. Further, a nickel oxide or cobalt oxide thin film formed by using the diazadiene-based nickel or cobalt compound in accordance with the present disclosure may be used as a memory substance or a sensor. Further, a manganese oxide thin film formed by using the diazadiene-based manganese in accordance with the present disclosure may be used as a copper diffusion barrier film or the like.

BEST MODE FOR CARRYING OUT THE INVENTION

Figure 1:
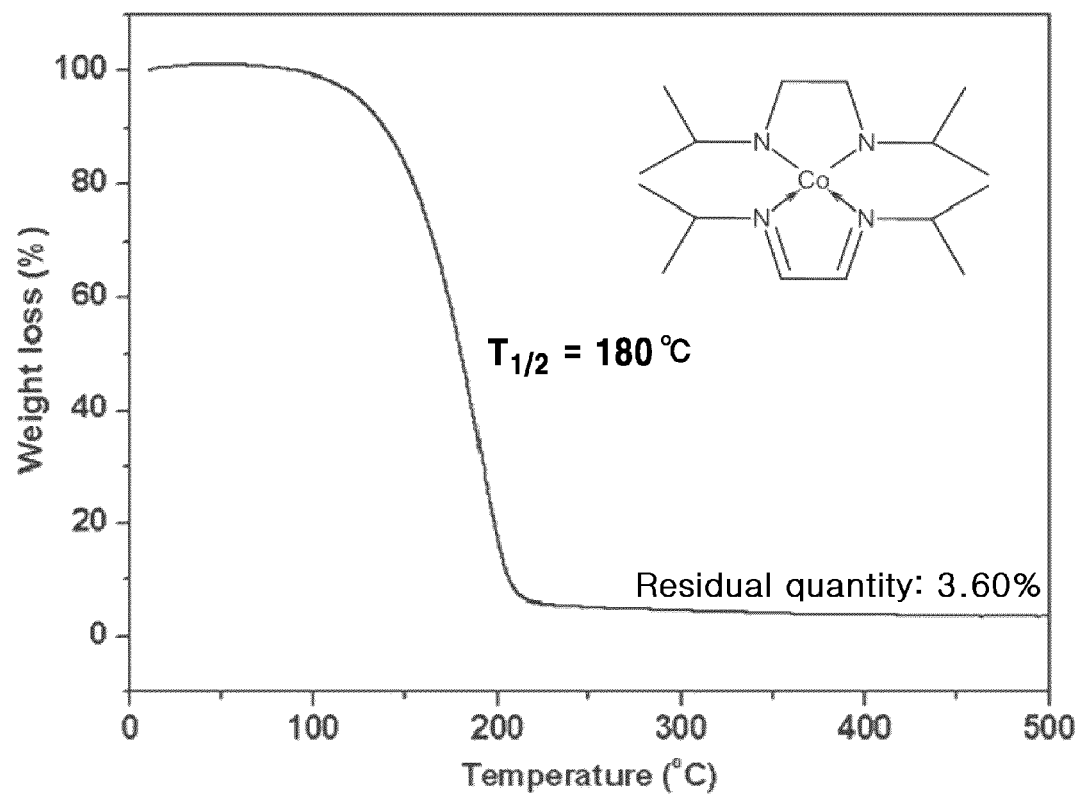
FIG. 1 is a TGA (Thermo Gravimetric Analysis) graph of a cobalt compound synthesized in Example 1 of the present disclosure.
Figure 2:
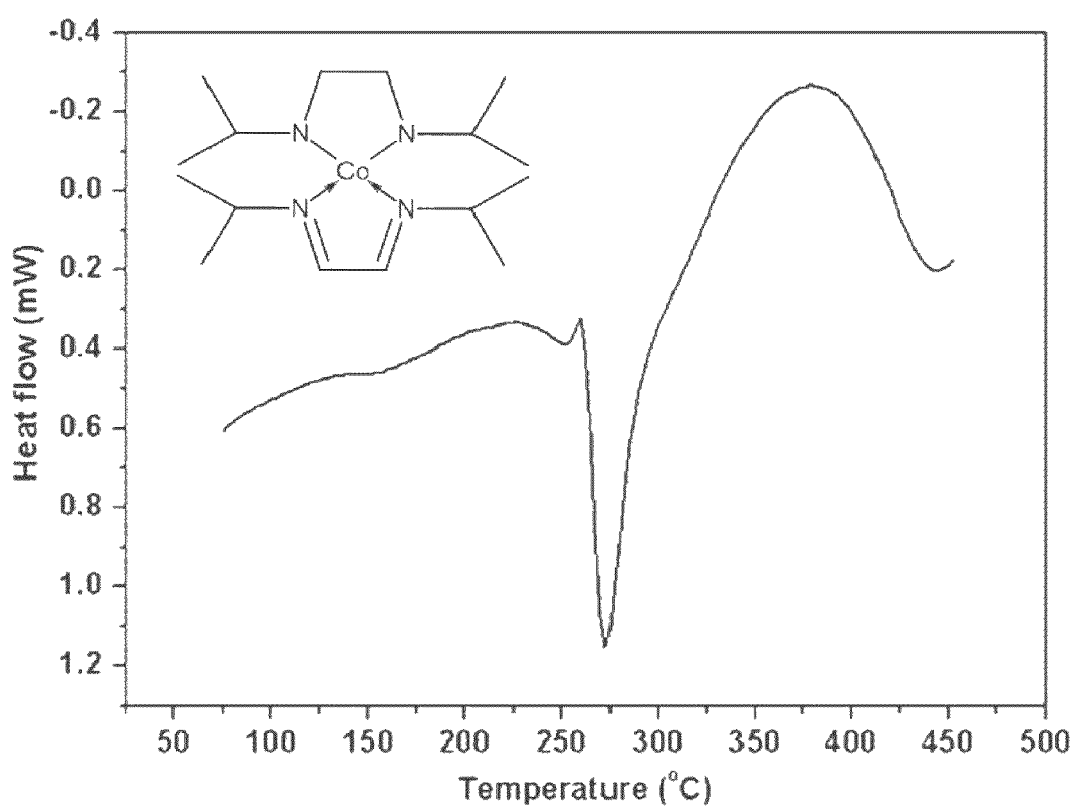
FIG. 2 is a DSC (Differential Scanning calorimetry) graph of the cobalt compound synthesized Example 1 of the present disclosure.
Figure 3:
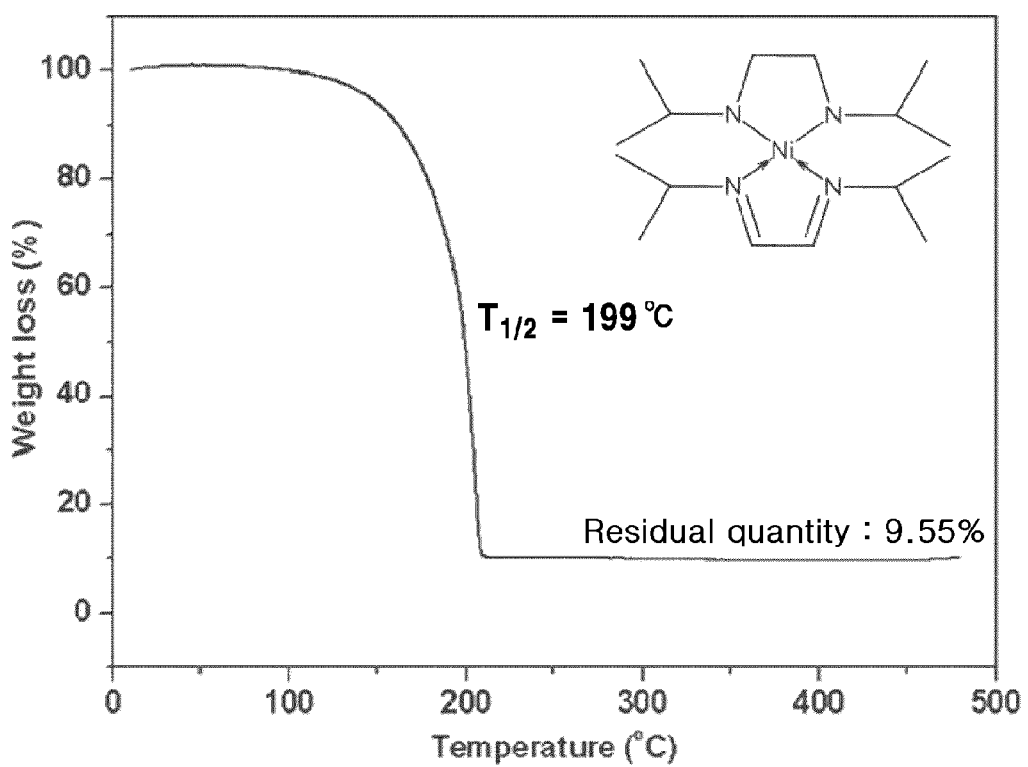
FIG. 3 is a TGA graph of a nickel compound synthesized in Example 5 of the present disclosure.
Figure 4:
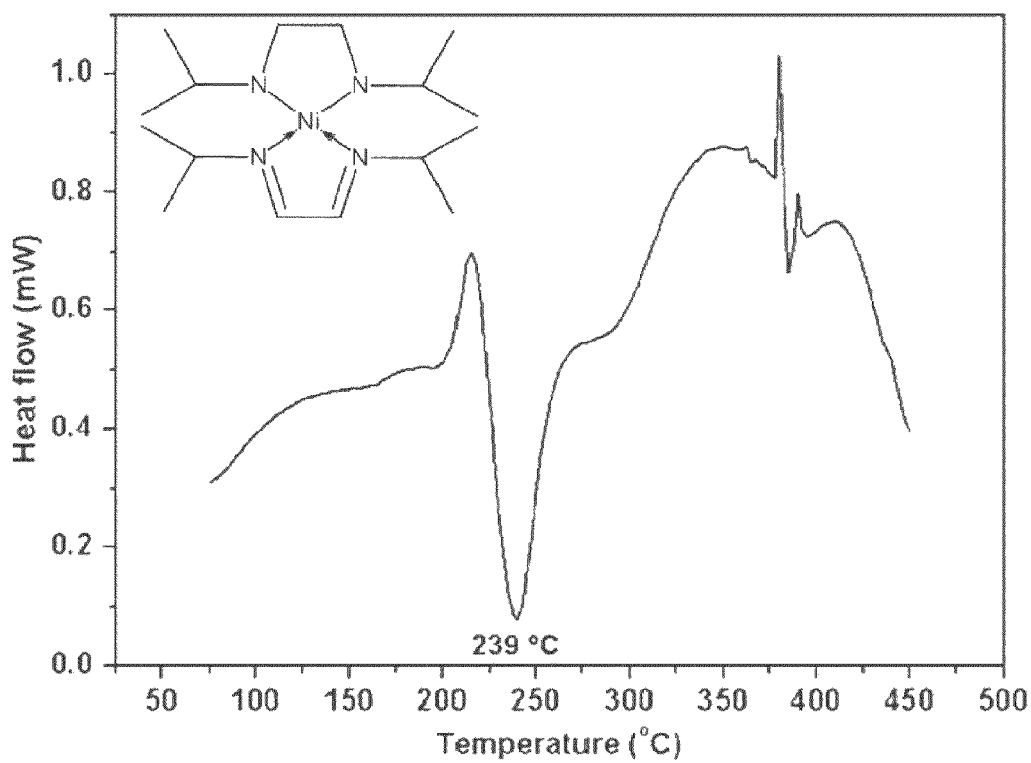
FIG. 4 is a DSC graph of the nickel compound synthesized in Example 5 of the present disclosure.
Figure 5:
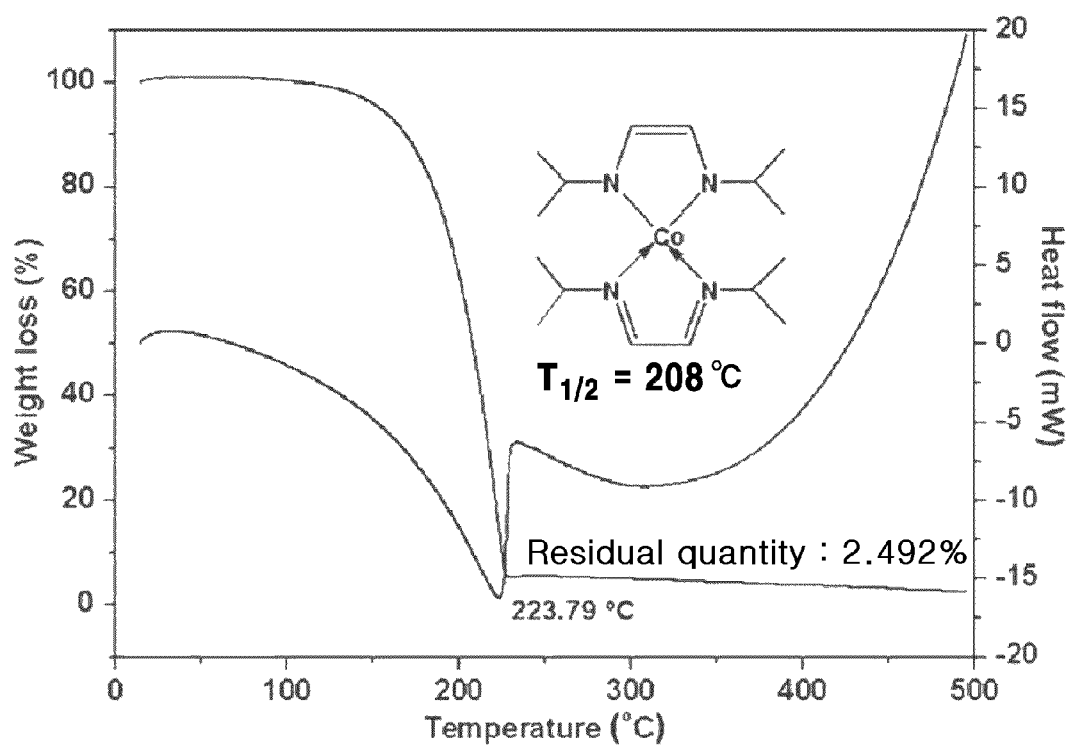
FIG. 5 provides a TGA/DSC graph of a cobalt compound synthesized in Example 9 of the present disclosure.
Figure 6:
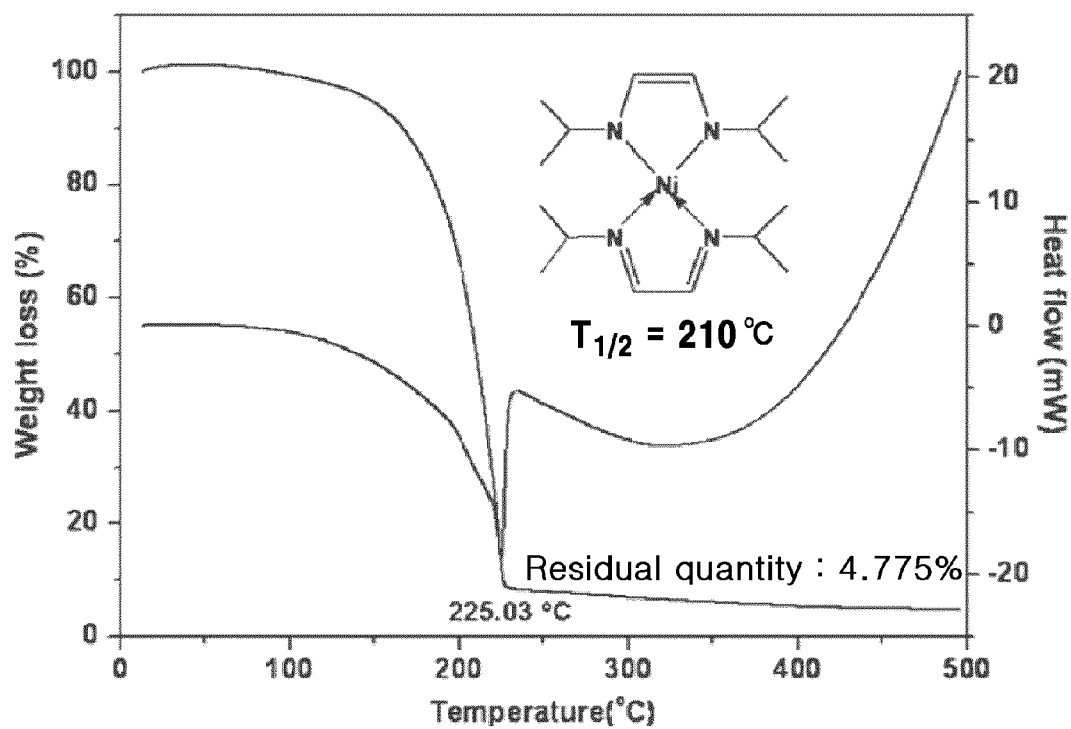
FIG. 6 is a TGA/DSC graph of a nickel compound synthesized in Example 11 of the present disclosure.
Figure 7:
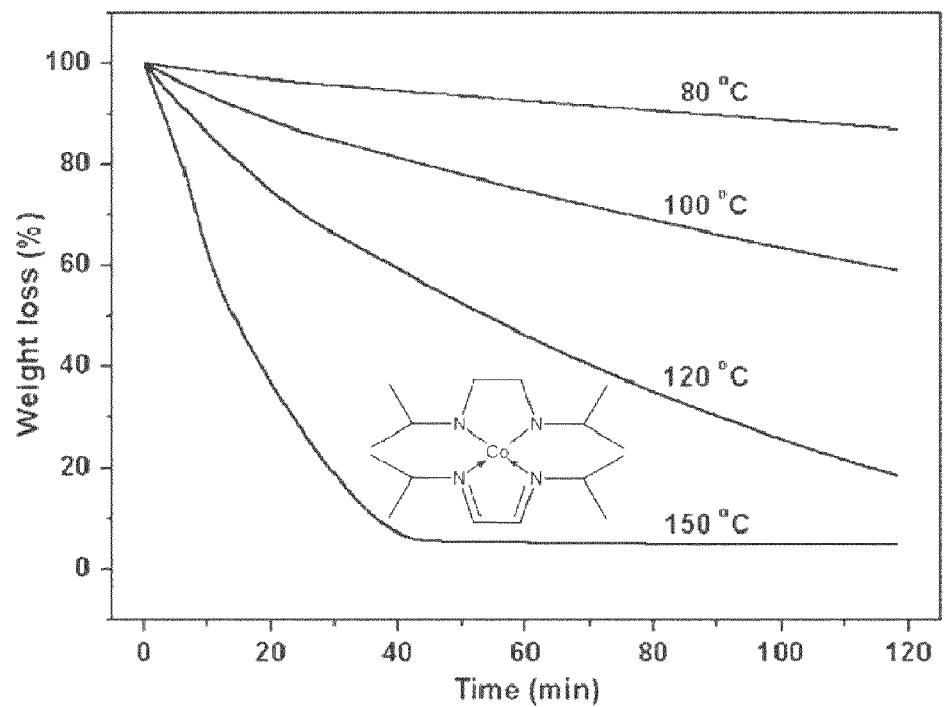
FIG. 7 is an isothermal TGA graph of the cobalt compound synthesized in Example 1 of the present disclosure.
Figure 8:
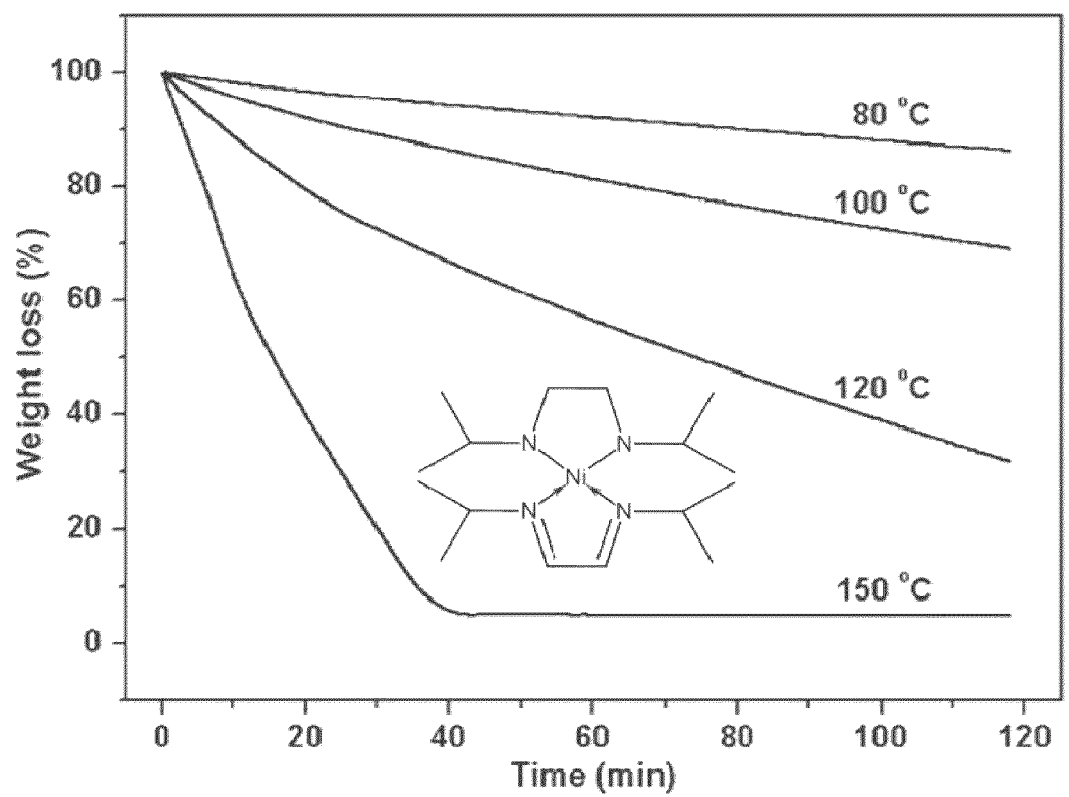
FIG. 8 is an isothermal TGA graph of the nickel compound synthesized in Example 5 of the present disclosure.
Figure 9:
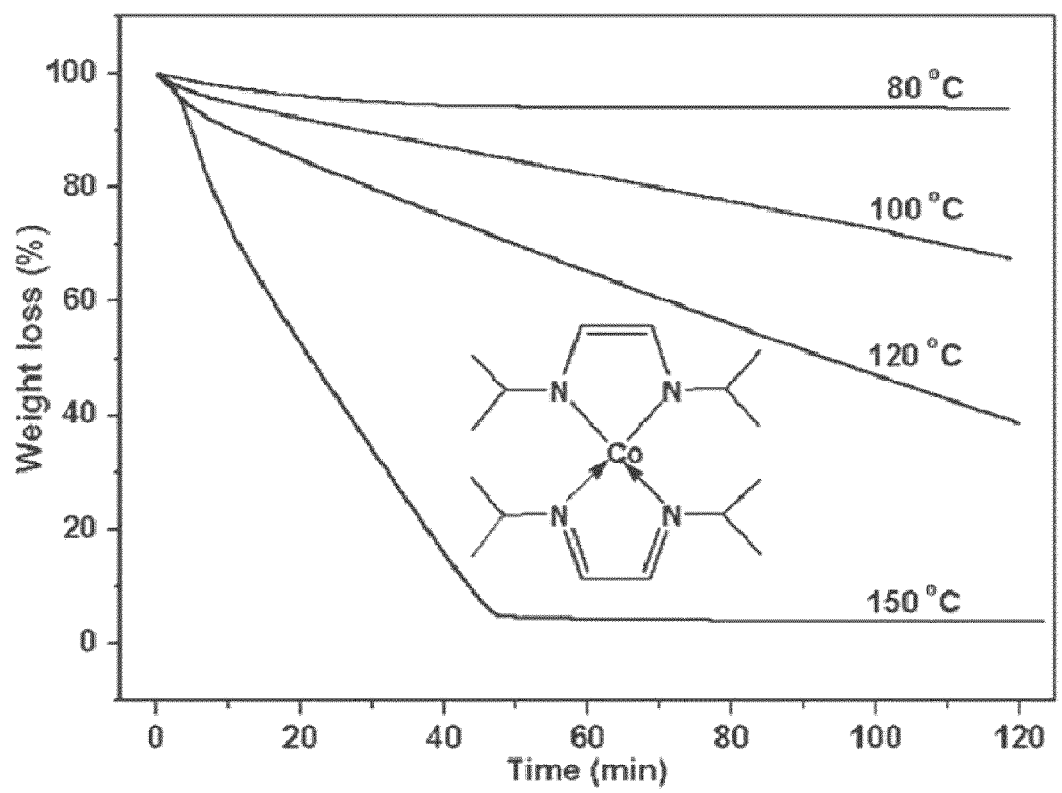
FIG. 9 is an isothermal TGA graph of the cobalt compound synthesized in Example 9 of the present disclosure.
Figure 10:
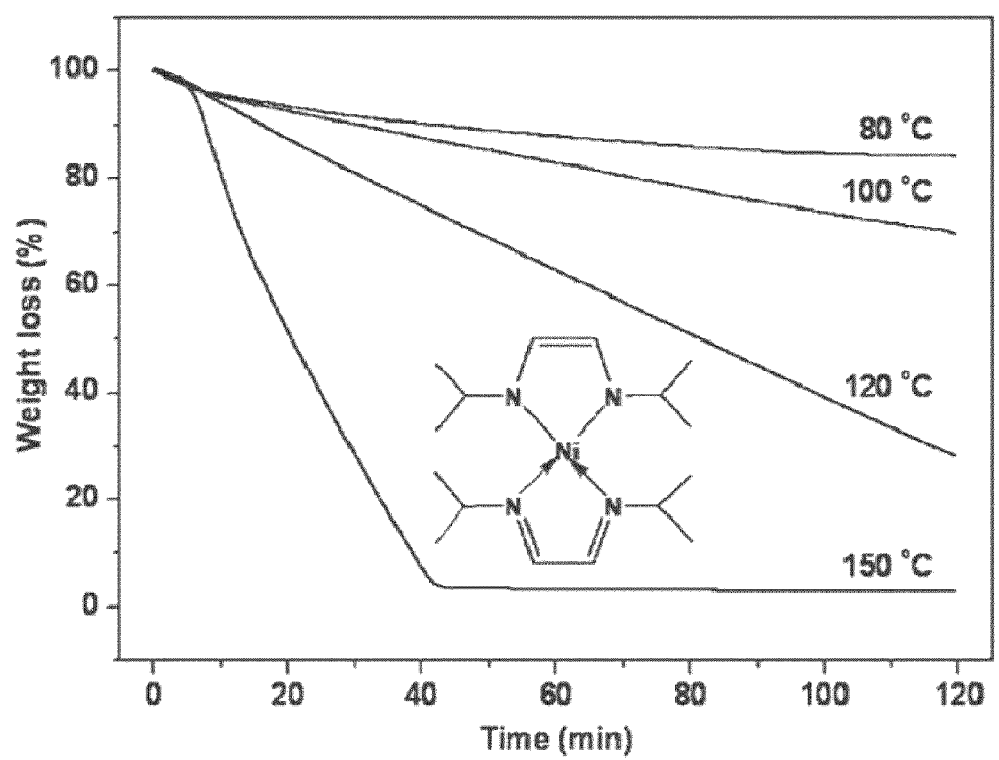
FIG. 10 is an isothermal TGA graph of the nickel compound synthesized in Example 11 of the present disclosure.

Hereinafter, illustrative embodiments and examples will be described in detail so that inventive concept may be readily implemented by those skilled in the art.

However, it is to be noted that the present disclosure is not limited to the illustrative embodiments and examples but can be realized in various other ways. In drawings, parts not directly relevant to the description are omitted to enhance the clarity of the drawings, and like reference numerals denote like parts through the whole document.

Through the whole document, the term "on" that is used to designate a position of one element with respect to another element includes both a case that the one element is adjacent to the another element and a case that any other element exists between these two elements.

Through the whole document, the term "comprises or includes" and/or "comprising or including" used in the document means that one or more other components, steps, operation and/or existence or addition of elements are not excluded in addition to the described components, steps, operation and/or elements unless context dictates otherwise.

The term "about or approximately" or "substantially" are intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination of" included in Markush type description means mixture or combination of one or more components, steps, operations and/or elements selected from the group consisting of components, steps, operation and/or elements described in Markush type and thereby means that the disclosure includes one or more components, steps, operations and/or elements selected from the Markush group.

Through the whole document, unless otherwise defined, the term "alkyl" may include, when used alone or used together with other terms such as "alkoxy," "arylalkyl," "alkanolamine," and "alkoxyamine," a linear or branched alkyl group having carbon atoms in a number ranging from about 1 to about 22, or about 1 to about 20, or about 1 to about 12, or about 1 to about 10, or about 1 to about 6. By way of example, the alkyl may be methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and their isomers etc., but may not be limited thereto.

Below, illustrative embodiments and examples of a diazadiene-based metal compound, a preparing method therefor and a method for forming a thin film using the diazadiene-based metal compound will be described in detail with reference to the accompanying drawings. However, it should be noted that the illustrative embodiments and examples are nothing more than examples and the present disclosure may not be limited thereto.

A diazadiene-based metal compound in accordance with the first aspect of the present disclosure may be represented by the following chemical formulas 1 to 4.

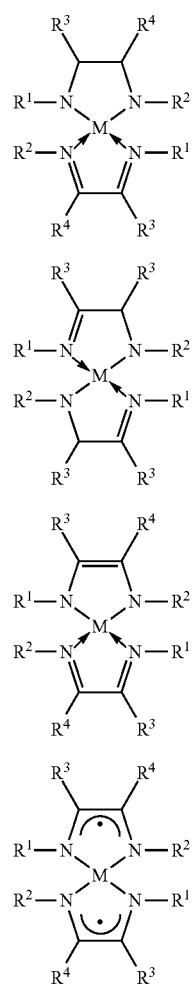

<Chemical formula 1>

<Chemical formula 2>

<Chemical formula 3>

<Chemical formula 4>

In the above chemical formulas 1 to 4,
M denotes Ni, Co or Mn, and
each of $R^1$ to $R^4$ represents independently hydrogen, or a linear or branched alkyl group having a carbon number ranging from about 1 to about 6.

In accordance with an illustrative embodiment, the diazadiene-based metal compound may be represented by the chemical formula 1, in which $R^1$ and $R^2$ are iso-propyl groups or tert-butyl groups, and $R^3$ and $R^4$ are hydrogen, but may not be limited thereto.

In accordance with an illustrative embodiment, the diazadiene-based metal compound may be represented by the chemical formula 2, in which $R^1$ and $R^2$ are iso-propyl groups or tert-butyl groups, and $R^3$ is hydrogen, but may not be limited thereto.

In accordance with an illustrative embodiment, the diazadiene-based metal compound may be represented by the chemical formula 3, in which $R^1$ and $R^2$ are iso-propyl groups or tert-butyl groups, and $R^3$ and $R^4$ are hydrogen, but may not be limited thereto.

In accordance with an illustrative embodiment, the diazadiene-based metal compound may be represented by the chemical formula 4, in which $R^1$ and $R^2$ are iso-propyl groups or tert-butyl groups, and $R^3$ and $R^4$ are hydrogen, but may not be limited thereto.

In accordance with an illustrative embodiment, in the chemical formulas 1 to 4, both of $R^1$ and $R^2$ are iso-propyl (isopropyl, $^iPr$) groups or tert-butyl (tertiary butyl, $^tBu$) groups, but may not be limited thereto. Especially, diazadiene-based Ni, Co or Mn compounds having structures as illustrated below in which $R^1$ and $R^2$ are $^iPr$ groups or $^tBu$ groups, and $R^3$ and $R^4$ are hydrogen have high vapor pressures. Thus, it may be advantageous to use these diazadiene-based Ni, Co or Mn compounds in chemical deposition or atomic layer deposition.

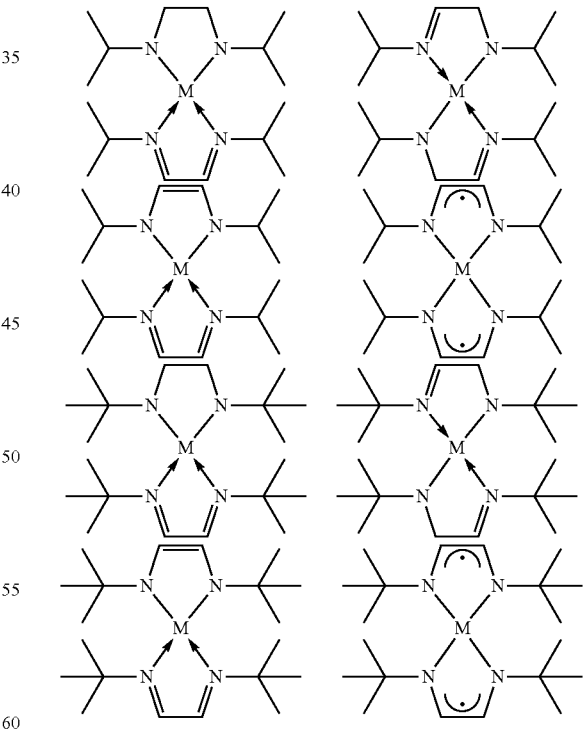

In accordance with a second aspect of the present disclosure, there is provided a method for preparing a diazadiene-based metal compound, as indicated by the following reaction formula 1, including reacting a diazadiene neutral ligand represented by the following chemical formula 5 with a hydrogen reducing agent to synthesize diazadiene-induced bivalent negative ions; and reacting the diazadiene neutral ligand represented by the following chemical formula 5 with a bivalent halogen metal compound represented by $MX_2$ and then adding the diazadiene-induced bivalent negative ions thereto to thereby allow a reaction therebetween.

sented by the following chemical formula 6 with a hydrogen reducing agent to synthesize a diazadiene-induced monovalent negative ion; and adding a bivalent halogen metal compound represented by $MX_2$ to the diazadiene-induced monovalent negative ion to allow a reaction therebetween.

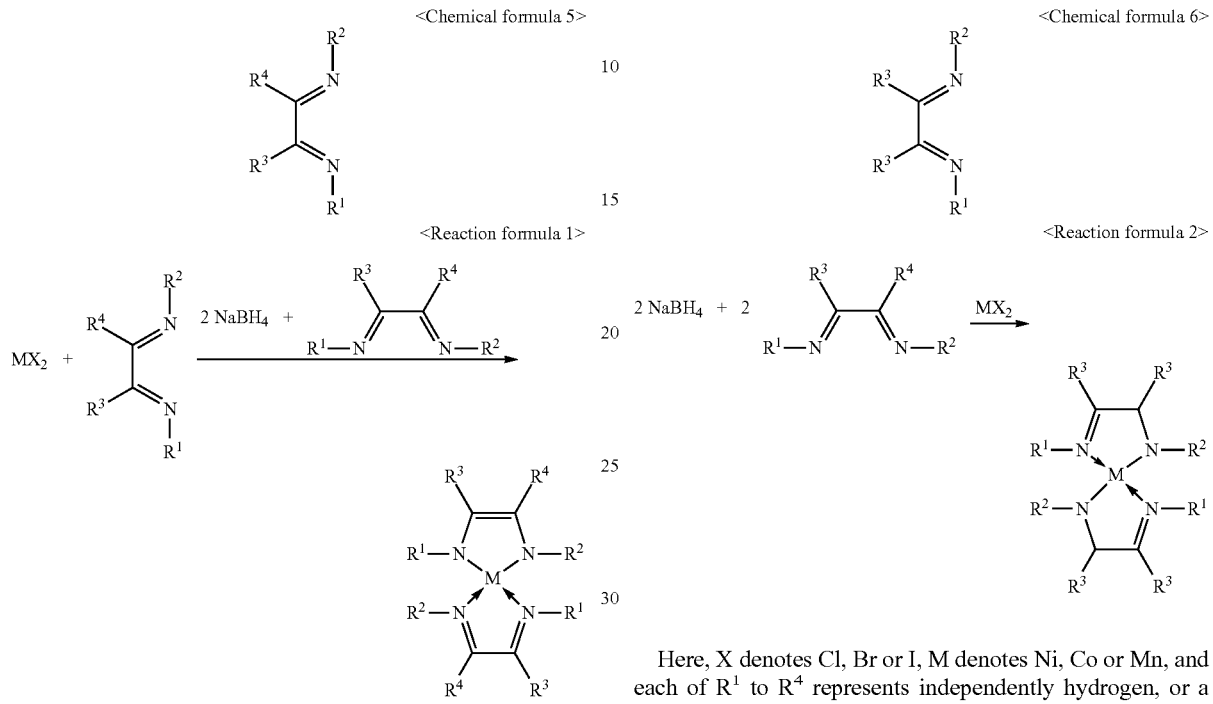

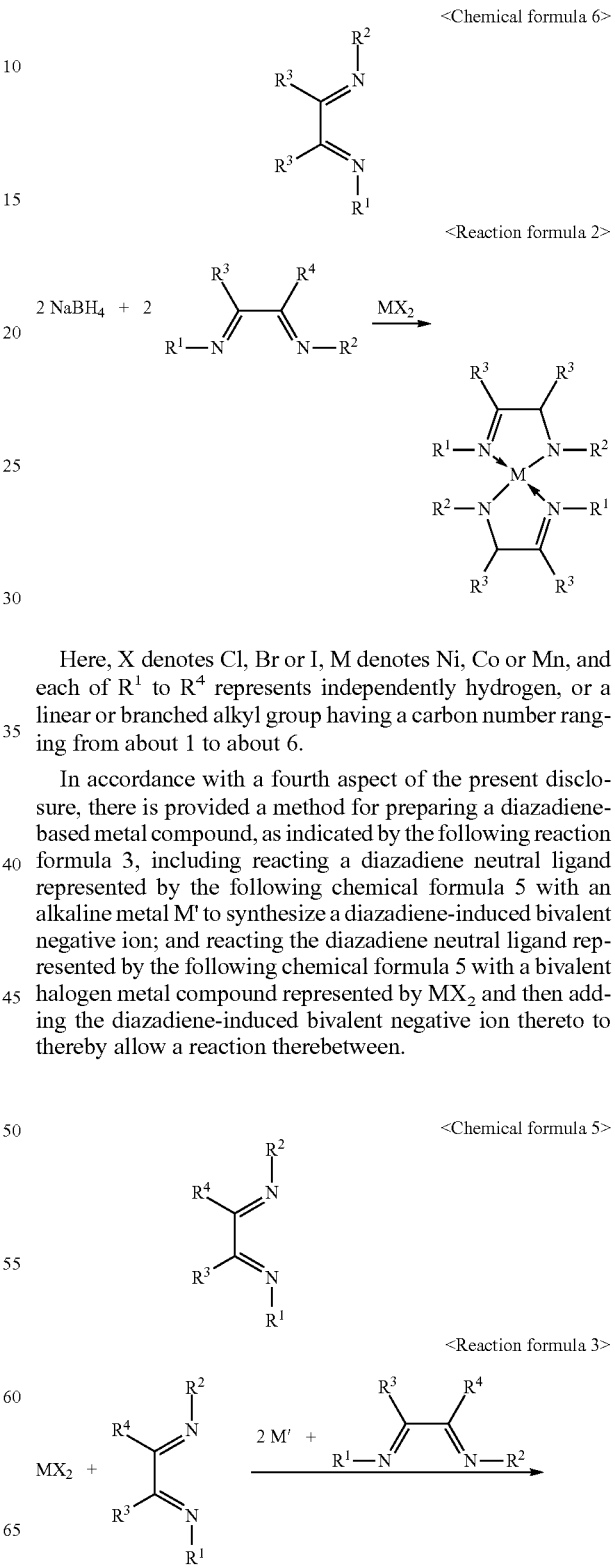

Here, X denotes Cl, Br or I, M denotes Ni, Co or Mn, and each of $R^1$ to $R^4$ represents independently hydrogen, or a linear or branched alkyl group having a carbon number ranging from about 1 to about 6.

To elaborate, for example, a diazadiene-based metal compound may be prepared as follows. A solution, which is prepared by adding $MX_2$ and diazadiene neutral ligand to an organic solvent (here, $MX_2$ may be dissolved in the solvent, or may be dispersed in the solvent in the form of powder), is cooled to a temperature of −30° C. to about 0° C. Then, the bivalent negative solution obtained by allowing the hydrogen reducing agent to react with the diazadiene neutral ligand is added gradually. Then, after stirring the mixture, salt that that is not dissolved in the organic solvent is filtered and the organic solvent is removed. Through this process, the diazadiene-based metal compound can be prepared.

The organic solvent may not be particularly limited as long as it is a nonpolar organic solvent or an organic solvent having weak polarity. By way of non-limiting example, tetrahydrofuran (THF), 1,2-dimethoxyethane, 2-methoxyethyl ether or the like may be used. During the stirring reaction, in order to prevent decomposition that might by caused by water vapor, oxygen or the like in the middle of the reaction, the reaction may be performed under an atmosphere of an inert gas such as nitrogen ($N_2$) or argon (Ar), but may not be limited thereto.

The hydrogen reducing agent may use, $NaBH_4$, $LiAlH_4$, $(n-Bu)_3SnH$, or the like, besides LiH, NaH, KH, but may not be limited thereto (here, n-Bu denotes a normal butyl group).

In accordance with a third aspect of the present disclosure, there is provided a method for preparing a diazadiene-based metal compound, as indicated by the following reaction formula 2, including reacting a diazadiene neutral ligand repre- Here, X denotes Cl, Br or I, M denotes Ni, Co or Mn, and each of $R^1$ to $R^4$ represents independently hydrogen, or a linear or branched alkyl group having a carbon number ranging from about 1 to about 6.

In accordance with a fourth aspect of the present disclosure, there is provided a method for preparing a diazadiene-based metal compound, as indicated by the following reaction formula 3, including reacting a diazadiene neutral ligand represented by the following chemical formula 5 with an alkaline metal M' to synthesize a diazadiene-induced bivalent negative ion; and reacting the diazadiene neutral ligand represented by the following chemical formula 5 with a bivalent halogen metal compound represented by $MX_2$ and then adding the diazadiene-induced bivalent negative ion thereto to thereby allow a reaction therebetween.

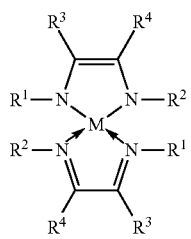

Here, M' denotes Li, Na or K, X denotes Cl, Br or I, M denotes Ni, Co or Mn, and each of $R^1$ to $R^4$ represents independently hydrogen, or a linear or branched alkyl group having a carbon number ranging from about 1 to about 6.

In accordance with a fifth aspect of the present disclosure, there is provided a method for preparing a diazadiene-based metal compound, as indicated by the following reaction formula 4, including reacting a diazadiene neutral ligand represented by the following chemical formula 5 with an alkaline metal M' to synthesize diazadiene-induced monovalent negative ion; and adding a bivalent halogen metal compound represented by $MX_2$ to the diazadiene-induced monovalent negative ion to thereby allow a reaction therebetween.

<Chemical formula 5>

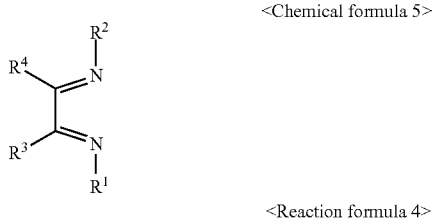

<Reaction formula 4>

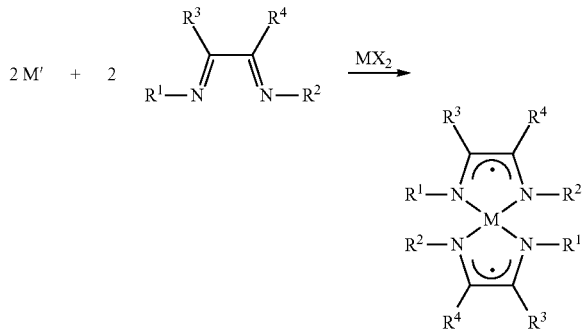

Here, M' denotes Li, Na or K, X denotes Cl, Br or I, M denotes Ni, Co or Mn, and each of $R^1$ to $R^4$ represents independently hydrogen, or a linear or branched alkyl group having a carbon number ranging from about 1 to about 6.

In accordance with a sixth aspect of the present disclosure, there is provided a thin film forming method, including depositing a diazadiene-based metal compound represented by one of the above chemical formulas 1 to 4 used as a source material on a substrate by chemical vapor deposition or atomic layer deposition to form a metal thin film containing nickel, cobalt or manganese, but may not be limited thereto.

In accordance with an illustrative embodiment, the diazadiene-based metal compound may be in a gaseous state, but may not be limited thereto.

In accordance with an illustrative embodiment, when depositing the thin film on the substrate by chemical deposition or atomic layer deposition while using the diazadiene-based metal compound as a precursor, a deposition temperature may range, but may not be limited to, from about 50° C. to about 700° C. By way of example, the deposition temperature may range, from about 50° C. to about 700° C., from about 50° C. to about 600° C., from about 50° C. to about 500° C., from about 50° C. to about 400° C., from about 50° C. to about 300° C., from about 50° C. to about 200° C., or from about 50° C. to about 100° C., but may not be limited thereto.

In order to deliver the diazadiene-based metal compound onto the surface of the substrate in the gaseous state, various supply methods such as a bubbling method, a vapor phase mass flow controller (MFC) method, a direct liquid injection (DLI) method, or a liquid delivery system (LDS) may be used, but may not be limited thereto. In the DLI, the precursor compound is delivered while dissolved in an organic solvent.

Argon, nitrogen, helium (He), hydrogen ($H_2$) or a gaseous mixture thereof may be used as a carrier gas for supplying the diazadiene-based metal compound or as a purge gas in the atomic layer deposition method, but may not be limited thereto. In order to deposit a thin film of metal oxide by the chemical vapor deposition and atomic layer deposition, water vapor ($H_2O$), oxygen ($O_2$) or ozone ($O_3$) may be used as a reactant gas, but may not be limited thereto. Besides, in order to form a thin film of a metal, a metal silicide or a metal oxide, hydrogen, ammonia ($NH_3$), alcohols, aldehydes, carboxylic acids and silanes may be used as a reactant gas, but may not be limited thereto.

Below, examples of the illustrative embodiment will be described. However, the following examples are intended to facilitate understanding of the present disclosure and therefore are not intended to limit its scope.

EXAMPLES

Example 1

Synthesis of the Organic Cobalt Precursor Represented by Chemical Formula 7

In a 250 mL of flame-dried Schlenk flask, a suspension was prepared by dissolving 10 g (77 mmol, 1 equivalent weight) of anhydrous $CoCl_2$ and 10.80 g (77 mmol, 1.0 equivalent weight) of N,N'-diisopropyl-1,4-diaza-1,3-butadiene ($^i$Pr-DAD) in 50 mL of 2-methoxyethyl ether. The flask storing the suspension therein was maintained at a temperature of −20° C. Then, after a solution prepared by dissolving 10.80 g (77 mmol, 1.0 equivalent weight) of $^i$Pr-DAD and 5.83 g (154 mmol, 2.0 equivalent weight) of $NaBH_4$ in 70 mL of 2-methoxyethyl ether was slowly added to the flask maintained at the temperature of −20° C., the temperature of the reaction solution in the flask was slowly raised to a room temperature. After stirring this mixture solution at the room temperature for 12 hours, solvent and a volatile by-product were removed from the mixture solution under reduced pressure. Then, 200 mL of normal hexane (n-hexane, $C_6H_{14}$) was added and the mixture was dissolved therein. Thereafter, under reduced pressure, the normal hexane used as the solvent was removed from a filtrate obtained by filtering the mixture dissolved in the normal hexane through a cellite pad and a glass frit, and, then, vacuum distillation was performed. As a result, a yellowish brown liquid compound represented by the following chemical formula 7 was obtained:

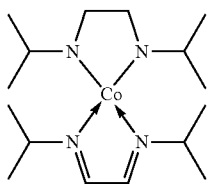

<Chemical formula 7>

Yield: 11.12 g (42.3%),
Elemental analysis ($C_{16}H_{34}N_4Co$): calculated values (C, 56.29; H, 10.04; N, 16.41), Measurement values (C, 56.22; H, 9.68; N, 16.56),
Boiling point: 75° C. at 0.32 torr,
Density: 1.203 g/mL, 25° C.

Example 2

Synthesis of the Organic Cobalt Precursor Represented by Chemical Formula 8

In a 250 mL of flame-dried Schlenk flask, a suspension was prepared by dissolving 10 g (77 mmol, 1 equivalent weight) of anhydrous $CoCl_2$ in 50 mL of 2-methoxyethyl ether. The flask storing the suspension therein was maintained at a temperature of −20° C. Then, after a solution prepared by dissolving 5.83 g (154 mmol, 2.0 equivalent weight) of $NaBH_4$ and 21.60 g (154 mmol, 2.0 equivalent weight) of $^iPr$-DAD in 70 mL of 2-methoxyethyl ether was slowly added to the flask maintained at the temperature of −20° C., the temperature of the reaction solution in the flask was slowly raised to a room temperature. After stirring this mixture solution at the room temperature for 12 hours, solvent and a volatile by-product were removed from the mixture solution under reduced pressure. Then, 200 mL of normal hexane (n-hexane, $C_6H_{14}$) was added and the mixture was dissolved therein. Thereafter, under reduced pressure, the normal hexane used as the solvent was removed from a filtrate obtained by filtering the mixture dissolved in the normal hexane through a cellite pad and a glass frit, and, then, vacuum distillation was performed. As a result, a yellowish brown liquid compound represented by the following chemical formula 8 was obtained:

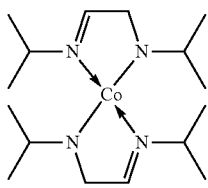

<Chemical formula 8>

Yield: 10.54 g (40.1%),
Elemental analysis ($C_{16}H_{34}N_4Co$): calculated values (C, 56.29; H, 10.04; N, 16.41), Measurement values (C, 55.98; H, 10.8; N, 16.39),
Boiling point: 76° C. at 0.32 torr,
Density: 1.206 g/mL, 25° C.

Example 3

Synthesis of the Organic Cobalt Precursor Represented by Chemical Formula 9

In a 250 mL of flame-dried Schlenk flask, a suspension was prepared by dissolving 10 g (77 mmol, 1 equivalent weight) of anhydrous $CoCl_2$ and 12.96 g(77 mmol, 1.0equivalent weight) of N,N'-di-tert-butyl-1,4-diaza-1,3-butadiene (tBu-DAD) in 50 mL of 2-methoxyethyl ether. The flask storing the suspension therein was maintained at a temperature of −20° C. Then, after a solution prepared by dissolving 12.96 g (77 mmol, 1.0 equivalent weight) of tBu-DAD and 5.83 g (154 mmol, 2.0 equivalent weight) of $NaBH_4$ in 70 mL of 2-methoxyethyl ether was slowly added to the flask maintained at the temperature of −20° C., the temperature of the reaction solution in the flask was slowly raised to a room temperature. After stirring this mixture solution at the room temperature for 12 hours, solvent and a volatile by-product were removed from the mixture solution under reduced pressure. Then, 200 mL of normal hexane was added and the mixture was dissolved therein. Thereafter, under reduced pressure, the normal hexane used as the solvent was removed from a filtrate obtained by filtering the mixture dissolved in the normal hexane through a cellite pad and a glass frit, and, then, sublimation purification was performed. As a result, a yellowish brown solid compound represented by the following chemical formula 9 was obtained:

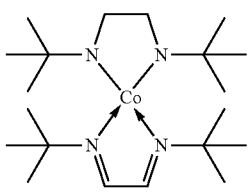

<Chemical formula 9>

Yield: 16.62 g (54.3%),
Elemental analysis ($C_{20}H_{42}N_4Co$): calculated values (C, 60.43; H, 10.65; N, 14.09), Measurement values (C, 60.21; H, 10.61; N, 14.16),
Boiling point: 83° C. at 0.32 torr,
Density: 1.212 g/mL, 25° C.

Example 4

Synthesis of the Organic Cobalt Precursor Represented by Chemical Formula 10

In a 250 mL of flame-dried Schlenk flask, a suspension was prepared by dissolving 10 g (77 mmol, 1 equivalent weight) of anhydrous $CoCl_2$ in 50 mL of 2-methoxyethyl ether. The flask storing the suspension therein was maintained at a temperature of −20° C. Then, after a solution prepared by dissolving 5.83 g (154 mmol, 2.0 equivalent weight) of $NaBH_4$ and 25.92 g (154 mmol, 2.0 equivalent weight) of tBu-DAD in 70 mL of 2-methoxyethyl ether was slowly added to the flask maintained at the temperature of −20° C., the temperature of the reaction solution in the flask was slowly raised to a room temperature. After stirring this mixture solution at the room temperature for 12 hours, solvent and a volatile by-product were removed from the mixture solution under reduced pressure. Then, 200 mL of normal hexane (n-hexane, $C_6H_{14}$) was added and the mixture was dissolved therein. Thereafter, under reduced pressure, the normal hexane used as the solvent was removed from a filtrate obtained by filtering the mixture dissolved in the normal hexane through a cellite pad and a glass frit, and, then, sublimation purification was performed. As a result, a yellowish brown solid compound represented by the following chemical formula 10 was obtained:

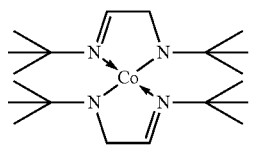

<Chemical formula 10>

Yield: 16.13 g (52.7%),

Elemental analysis ($C_{20}H_{42}N_4Co$): calculated values (C, 60.43; H, 10.65; N, 14.09), Measurement values (C, 60.32; H, 10.59; N, 14.01), Boiling point: 84° C. at 0.32 torr, Density: 1.213 g/mL, 25° C.

Example 5

Synthesis of the Organic Nickel Precursor Represented by Chemical Formula 11

In a 250 mL of flame-dried Schlenk flask, a suspension was prepared by dissolving 10 g (46 mmol, 1 equivalent weight) of anhydrous $NiBr_2$ and 6.42 g (46 mmol, 1.0 equivalent weight) of $^i$Pr-DAD in 50 mL of 2-methoxyethyl ether. The flask storing the suspension therein was maintained at a temperature of −20° C. Then, after a solution prepared by dissolving 6.42 g (46 mmol, 1.0 equivalent weight) of $^i$Pr-DAD and 3.46 g (92 mmol, 2.0 equivalent weight) of $NaBH_4$ in 70 mL of 2-methoxyethyl ether was slowly added to the flask maintained at the temperature of −20° C., the temperature of the reaction solution in the flask was slowly raised to a room temperature. After stirring this mixture solution at a room temperature for 12 hours, solvent and a volatile by-product were removed from the mixture solution under reduced pressure. Then, 200 mL of normal hexane was added and the mixture was dissolved therein. Thereafter, under reduced pressure, the normal hexane used as the solvent was removed from a filtrate obtained by filtering the mixture dissolved in the normal hexane through a cellite pad and a glass frit, and, then, vacuum distillation was performed. As a result, a wine-colored liquid compound represented by the following chemical formula 11 was obtained:

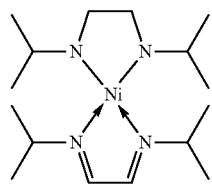

<Chemical formula 11>

Yield: 6.42 g (41.1%),

Elemental analysis ($C_{16}H_{34}N_4Ni$): calculated values (C, 56.33; H, 10.05; N, 16.42), Measurement values (C, 56.32; H, 9.88; N, 16.51), Boiling point: 75° C. at 0.32 torr, Density: 1.251 g/mL, 25° C.

Example 6

Synthesis of the Organic Nickel Precursor Represented by Chemical Formula 12

In a 250 mL of flame-dried Schlenk flask, a suspension was prepared by dissolving 10 g (46 mmol, 1 equivalent weight) of anhydrous $NiBr_2$ in 50 mL of 2-methoxyethyl ether. The flask storing the suspension therein was maintained at a temperature of −20° C. Then, after a solution prepared by dissolving 3.46 g (92 mmol, 2.0 equivalent weight) of $NaBH_4$ and 12.84 g (92 mmol, 2.0. equivalent weight) of $^i$Pr-DAD in 70 mL of 2-methoxyethyl ether was slowly added to the flask maintained at the temperature of −20° C., the temperature of the mixture solution in the flask was slowly raised to a room temperature. After stirring this mixture solution at a room temperature for 12 hours, solvent and a volatile by-product were removed from the mixture solution under reduced pressure. Then, 200 mL of normal hexane (n-hexane, $C_6H_{14}$) was added and the mixture was dissolved therein. Thereafter, under reduced pressure, the normal hexane used as the solvent was removed from a filtrate obtained by filtering the mixture dissolved in the normal hexane through a cellite pad and a glass frit, and, then, vacuum distillation was performed. As a result, a wine-colored liquid compound represented by the following chemical formula 12 was obtained:

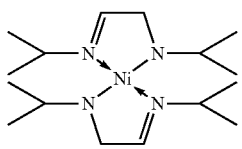

<Chemical formula 12>

Yield: 6.15 g (39.4%),

Elemental analysis ($C_{16}H_{34}N_4Ni$): calculated values (C, 56.33; H, 10.05; N, 16.42), Measurement values (C, 56.21; H, 10.01; N, 16.37), Boiling point: 76° C. at 0.32 torr, Density: 1.253 g/mL, 25° C.

Example 7

Synthesis of the Organic Nickel Precursor Represented by Chemical Formula 13

In a 250 mL of flame-dried Schlenk flask, a suspension was prepared by dissolving 10 g (46 mmol, 1 equivalent weight) of anhydrous $NiBr_2$ and 7.70 g (46 mmol, 1.0 equivalent weight) of $^t$Bu-DAD in 50 mL of 2-methoxyethyl ether. The flask storing the suspension therein was maintained at a temperature of −20° C. Then, after a solution prepared by dissolving 7.70 g (46 mmol, 1.0 equivalent weight) of $^t$Bu-DAD and 3.46 g (92 mmol, 2.0 equivalent weight) of $NaBH_4$ in 70 mL of 2-methoxyethyl ether was slowly added to the flask maintained at the temperature of −20° C., the temperature of the reaction solution in the flask was slowly raised to a room temperature. After stirring this mixture solution at the room temperature for 12 hours, solvent and a volatile by-product were removed from the mixture solution under reduced pressure. Then, about 200 mL of normal hexane was added and the mixture was dissolved therein. Thereafter, under reduced pressure, the normal hexane used as the solvent was removed from a filtrate obtained by filtering the mixture dissolved in the normal hexane through a cellite pad and a glass frit, and, then, sublimation purification was performed. As a result, a wine-colored solid compound represented by the following chemical formula 13 was obtained:

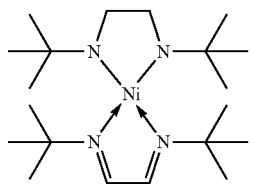

<Chemical formula 13>

Yield: 9.67 g (53.2%),
Elemental analysis ($C_{20}H_{42}N_4Ni$): calculated values (C, 60.47; H, 10.66; N, 14.10), Measurement values (C, 60.39; H, 10.57; N, 14.06),
Boiling point: 85° C. at 0.32 torr,
Density: 1.262 g/mL, 25° C.

Example 8

Synthesis of the Organic Nickel Precursor Represented by Chemical Formula 14

In a 250 mL of flame-dried Schlenk flask, a suspension was prepared by dissolving 10 g (46 mmol, 1 equivalent weight) of anhydrous $NiBr_2$ in 50 mL of 2-methoxyethyl ether. The flask storing the suspension therein was maintained at a temperature of −20° C. Then, after a solution prepared by dissolving 3.46 g (92 mmol, 2.0 equivalent weight) of $NaBH_4$ and 15.40 g (92 mmol, 2.0 equivalent weight) of $^t$Bu-DAD in 70 mL of 2-methoxyethyl ether was slowly added to the flask maintained at the temperature of −20° C., the temperature of the mixture solution in the flask was slowly raised to a room temperature. After stirring this mixture solution at the room temperature for 12 hours, solvent and a volatile by-product were removed from the mixture solution under reduced pressure. Then, 200 mL of normal hexane (n-hexane, $C_6H_{14}$) was added and the mixture was dissolved therein. Thereafter, under reduced pressure, the normal hexane used as the solvent was removed from a filtrate obtained by filtering the mixture dissolved in the normal hexane through a cellite pad and a glass frit, and, then, sublimation purification was performed. As a result, a wine-colored solid compound represented by the following chemical formula 14 was obtained:

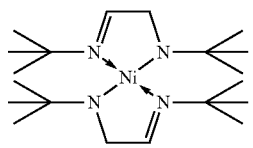

<Chemical formula 14>

Yield: 9.36 g (51.5%),
Elemental analysis ($C_{20}H_{42}N_4Ni$): calculated values (C, 60.47; H, 10.66; N, 14.10), Measurement values (C, 60.51; H, 10.69; N, 14.12),
Boiling point: 85° C. at 0.32 torr,
Density: 1.264 g/mL, 25° C.

Example 9

Synthesis of the Organic Cobalt Precursor Represented by Chemical Formula 15

In a 250 mL of flame-dried Schlenk flask, a suspension was prepared by dissolving 10 g (77 mmol, 1 equivalent weight) of anhydrous $CoCl_2$ and 10.80 g (77 mmol, 1.0. equivalent weight) of $^i$Pr-DAD in 50 mL of THF. The flask storing the suspension therein was maintained at a temperature of −20° C. Then, after a solution prepared by dissolving 10.80 g (77 mmol, 1.0. equivalent weight) of $^i$Pr-DAD and 1.07 g (154 mmol, 2.0 equivalent weight) of lithium (Li) in 70 mL of THF was slowly added to the flask maintained at the temperature of −20° C., the temperature of the reaction solution in the flask was slowly raised to a room temperature. After stirring this mixture solution at a room temperature for 12 hours, solvent and a volatile by-product were removed from the mixture solution under reduced pressure. Then, 200 mL of normal hexane was added and the mixture was dissolved therein. Thereafter, under reduced pressure, the normal hexane used as the solvent was removed from a filtrate obtained by filtering the mixture dissolved in the normal hexane through a cellite pad and a glass frit, and, then, vacuum distillation was performed. As a result, a yellowish brown liquid compound represented by the following chemical formula 15 was obtained:

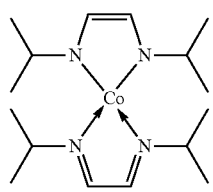

<Chemical formula 15>

Yield: 13.61 g (52.1%),
Elemental analysis ($C_{16}H_{32}N_4Co$): calculated values (C, 56.62; H, 9.50; N, 16.51), Measurement values (C, 56.32; H, 9.58; N, 16.61),
Boiling point: 80° C. at 0.25 torr,
Density: 1.092 g/mL, 25° C.

Example 10

Synthesis of the Organic Cobalt Precursor Represented by Chemical Formula 16

In a 250 mL of flame-dried Schlenk flask, a suspension was prepared by dissolving 10 g (77 mmol, 1 equivalent weight) of anhydrous $CoCl_2$ in 50 mL of THF. The flask storing the suspension therein was maintained at a temperature of −20° C. Then, after a solution prepared by dissolving 1.07 g (154 mmol, 2.0 equivalent weight) of lithium (Li) and 21.60 g (154 mmol, 2.0 equivalent weight) of $^i$Pr-DAD in 70 mL of THF was slowly added to the flask maintained at the temperature of −20° C., the temperature of the reaction solution in the flask was slowly raised to a room temperature. After stirring this mixture solution at a room temperature for 12 hours, solvent and a volatile by-product were removed from the mixture solution under reduced pressure. Then, 200 mL of normal hexane (n-hexane, $C_6H_{14}$) was added and the mixture was dissolved therein. Thereafter, under reduced pressure, the normal hexane used as the solvent was removed from a filtrate obtained by filtering the mixture dissolved in the normal hexane through a cellite pad and a glass frit, and, then, vacuum distillation was performed. As a result, a yellowish brown liquid compound represented by the following chemical Formula 16 was obtained:

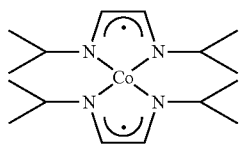

<Chemical formula 16>

Yield: 12.64 g (48.4%),
Elemental analysis ($C_{16}H_{32}N_4Co$): calculated values (C, 56.62; H, 9.50; N, 16.51), Measurement values (C, 55.99; H, 9.53; N, 16.48),
Boiling point: 80° C. at 0.25 torr,
Density: 1.113 g/mL, 25° C.

Example 11

Synthesis of the Organic Nickel Precursor Represented by Chemical Formula 17

In a 250 mL of flame-dried Schlenk flask, a suspension was prepared by dissolving 10 g (46 mmol, 1 equivalent weight) of anhydrous $NiBr_2$ and 6.42 g (46 mmol, 1.0 equivalent weight) of $^i$Pr-DAD in 50 mL of THF. The flask storing the suspension therein was maintained at a temperature of –20° C. Then, after a solution prepared by dissolving 6.42 g (46 mmol, 1.0 equivalent weight) of $^i$Pr-DAD and 0.64 g (92 mmol, 2.0 equivalent weight) of lithium (Li) in 70 mL of THF was slowly added to the flask maintained at the temperature of –20° C., the temperature of the reaction solution in the flask was slowly raised to a room temperature. After stirring this mixture solution at a room temperature for 12 hours, solvent and a volatile by-product were removed from the mixture solution under reduced pressure. Then, 200 mL of normal hexane was added and the mixture was dissolved therein. Thereafter, under reduced pressure, the normal hexane used as the solvent was removed from a filtrate obtained by filtering the mixture dissolved in the normal hexane through a cellite pad and a glass frit, and, then, vacuum distillation was performed. As a result, a wine-colored liquid compound represented by the following chemical formula 17 was obtained.

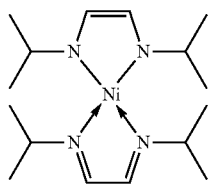

<Chemical formula 17>

Yield: 8.53 g (55.1%),
Elemental analysis ($C_{16}H_{32}N_4Ni$): calculated values (C, 56.66; H, 9.51; N, 16.52), Measurement values (C, 55.22; H, 9.58; N, 16.66),
Boiling point: 80° C. at 0.26 torr,
Density: 1.102 g/mL, 25° C.

Example 12

Synthesis of the Organic Nickel Precursor Represented by Chemical Formula 18

In a 250 mL of flame-dried Schlenk flask, a suspension was prepared by dissolving 10 g (46 mmol, 1 equivalent weight) of anhydrous $NiBr_2$ in 50 mL of THF. The flask storing the suspension therein was maintained at a temperature of –20° C. Then, after a solution prepared by dissolving 12.84 g (92 mmol, 2.0 equivalent weight) of $^i$Pr-DAD and 0.64 g (92 mmol, 2.0 equivalent weight) of lithium (Li) in 70 mL of THF was slowly added to the flask maintained at the temperature of –20° C., the temperature of the reaction solution in the flask was slowly raised to a room temperature. After stirring this mixture solution at a room temperature for 12 hours, solvent and a volatile by-product were removed from the mixture solution under reduced pressure. Then, 200 mL of normal hexane (n-hexane, $C_6H_{14}$) was added and the mixture was dissolved therein. Thereafter, under reduced pressure, the normal hexane used as the solvent was removed from a filtrate obtained by filtering the mixture dissolved in the normal hexane through a cellite pad and a glass frit, and, then, vacuum distillation was performed. As a result, a yellowish brown liquid compound represented by the following chemical formula 18 was obtained:

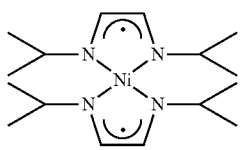

<Chemical formula 18>

Yield: 7.26 g (46.9%),
Elemental analysis ($C_{16}H_{32}N_4Ni$): calculated values (C, 56.66; H, 9.51; N, 16.52), Measurement values (C, 56.73; H, 9.56; N, 16.41),
Boiling point: 82° C. at 0.26 torr,
Density: 1.105 g/mL, 25° C.

Example 13

Synthesis of the Organic Manganese Precursor Represented by Chemical Formula 19

In a 250 mL of flame-dried Schlenk flask, a suspension was prepared by dissolving 10 g (79 mmol, 1 equivalent weight) of anhydrous $MnCl_2$, and 11.14 g (79 mmol, 1.0 equivalent weight) of $^i$Pr-DAD in 50 mL of 2-methoxyethyl ether. The flask storing the suspension therein was maintained at a temperature of –20° C. Then, after a solution prepared by dissolving 11.14 g (79 mmol, 1.0 equivalent weight) of $^i$Pr-DAD and 6.01 g (159 mmol, 2.0 equivalent weight) of $NaBH_4$ in 70 mL of 2-methoxyethyl ether was slowly added to the flask maintained at the temperature of –20° C., the temperature of the reaction solution in the flask was slowly raised to a room temperature. After stirring this mixture solution at a room temperature for 12 hours, solvent and a volatile by-product were removed from the mixture solution under reduced pressure. Then, 200 mL of normal hexane was added and the mixture was dissolved therein. Thereafter, under reduced pressure, the normal hexane used as the solvent was removed from a filtrate obtained by filtering the mixture dissolved in the normal hexane through a cellite pad and a glass frit, and, then, vacuum distillation was performed. As a result, a dark brown liquid compound represented by the following chemical formula 19 was obtained:

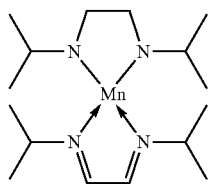

<Chemical formula 19>

Yield: 10.56 g (39.4%),
Elemental analysis ($C_{16}H_{34}N_4Mn$): calculated values (C, 56.96; H, 10.16; N, 16.61), Measurement values (C, 56.72; H, 10.21; N, 16.56),
Boiling point: 78° C. at 0.32 torr,
Density: 1.103 g/mL, 25° C.

Example 14

Synthesis of Organic Manganese Precursor Represented by Chemical Formula 20

In a 250 mL of flame-dried Schlenk flask, a suspension was prepared by dissolving 10 g (79 mmol, 1 equivalent weight) of anhydrous $MnCl_2$ in 50 mL of 2-methoxyethyl ether. The flask storing the suspension therein was maintained at a temperature of −20° C. Then, after a solution prepared by dissolving 6.01 g (159 mmol, 2.0 equivalent weight) of $NaBH_4$ and 22.29 g (159 mmol, 2.0 equivalent weight) of $^iPr$-DAD in 70 mL of 2-methoxyethyl ether was slowly added to the flask maintained at the temperature of −20° C., the temperature of the reaction solution in the flask was slowly raised to a room temperature. After stirring this mixture solution at a room temperature for 12 hours, solvent and a volatile by-product were removed from the mixture solution under reduced pressure. Then, about 200 mL of normal hexane (n-hexane, $C_6H_{14}$) was added and the mixture was dissolved therein. Thereafter, under reduced pressure, the normal hexane used as the solvent was removed from a filtrate obtained by filtering the mixture dissolved in the normal hexane through a cellite pad and a glass frit, and, then, vacuum distillation was performed. As a result, a dark brown liquid compound represented by the following chemical formula 20 was obtained:

<Chemical formula 20>

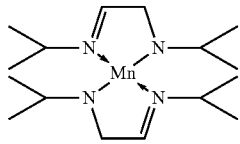

Yield: 10.08 g (37.6%),
Elemental analysis ($C_{16}H_{34}N_4Mn$): calculated values (C, 56.96; H, 10.16; N, 16.61), Measurement values (C, 56.84; H, 10.09; N, 16.63),
Boiling point: 78° C. at 0.32 torr,
Density: 1.105 g/mL, 25° C.

Example 15

Synthesis of Organic Manganese Precursor Represented by Chemical Formula 21

In a 250 mL of flame-dried Schlenk flask, a suspension was prepared by dissolving 10 g (79 mmol, 1 equivalent weight) of anhydrous $MnCl_2$ and 13.37 g (79 mmol, 1.0 equivalent weight) of $^tBu$-DAD in 50 mL of 2-methoxyethyl ether. The flask storing the suspension therein was maintained at a temperature of −20° C. Then, after a solution prepared by dissolving 13.37 g (79 mmol, 1.0 equivalent weight) of $^iPr$-DAD and 6.01 g (159 mmol, 2.0 equivalent weight) of $NaBH_4$ in 70 mL of 2-methoxyethyl ether was slowly added to the flask maintained at the temperature of −20° C., the temperature of the reaction solution in the flask was slowly raised to a room temperature. After stirring this mixture solution at a room temperature for 12 hours, solvent and a volatile by-product were removed from the mixture solution under reduced pressure. Then, about 200 mL of normal hexane was added and the mixture was dissolved therein. Thereafter, under reduced pressure, the normal hexane used as the solvent was removed from a filtrate obtained by filtering the mixture dissolved in the normal hexane through a cellite pad and a glass frit, and, then, vacuum distillation was performed. As a result, a dark brown solid compound represented by the following chemical formula 21 was obtained:

<Chemical formula 21>

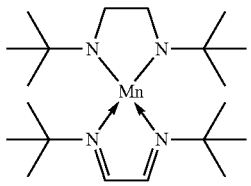

Yield: 16.45 g (52.6%),
Elemental analysis ($C_{20}H_{42}N_4Mn$): calculated values (C, 61.04; H, 10.76; N, 14.24), Measurement values (C, 61.12; H, 10.81; N, 14.36),
Boiling point: 84° C. at 0.32 torr,
Density: 1.223 g/mL, 25° C.

Example 16

Synthesis of the Organic Manganese Precursor Represented by Chemical Formula 22

In a 250 mL of flame-dried Schlenk flask, a suspension was prepared by dissolving 10 g (79 mmol, 1 equivalent weight) of anhydrous $MnCl_2$ in 50 mL of 2-methoxyethyl ether. The flask storing the suspension therein was maintained at a temperature of −20° C. Then, after a solution prepared by dissolving 6.01 g (159 mmol, 2.0 equivalent weight) of $NaBH_4$ and about 26.75 g (about 159 mmol, 2.0 equivalent weight) of $^tBu$-DAD in 70 mL of 2-methoxyethyl ether was slowly added to the flask maintained at the temperature of −20° C., the temperature of the reaction solution in the flask was slowly raised to a room temperature. After stirring this mixture solution at a room temperature for 12 hours, solvent and a volatile by-product were removed from the mixture solution under reduced pressure. Then, 200 mL of normal hexane (n-hexane, $C_6H_{14}$) was added and the mixture was dissolved therein. Thereafter, under reduced pressure, the normal hexane used as the solvent was removed from a filtrate obtained by filtering the mixture dissolved in the normal hexane through a cellite pad and a glass frit, and, then, vacuum distillation was performed. As a result, a dark brown liquid compound represented by the following chemical formula 22 was obtained:

<Chemical formula 22>

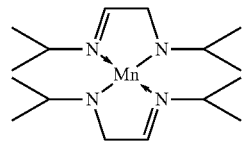

Yield: 16.04 g (51.3%),
Elemental analysis ($C_{20}H_{42}N_4Mn$): calculated values (C, 61.04; H, 10.76; N, 14.24), Measurement values (C, 60.99; H, 10.71; N, 14.19),
Boiling point: 85° C. at 0.32 torr,
Density: 1.225 g/mL, 25° C.

Experimental Example 1

Thermo Gravimetric Analysis and Differential Thermal Analysis

In order to analyze thermal characteristics of cobalt and nickel compounds represented by the chemical Formulas 7, 11, 15, and 17 and prepared in Examples 1, 5, 9, and 11, thermo gravimetric analysis (TGA) and differential scanning calorimetry (DSC) analysis were performed. At this time, about 5 mg of each of the samples was put into a sample vessel and a weight of each sample was measured in a temperature range up to 500° C. at a heating rate of 10° C./min. Measurement results are provided in FIGS. 1 to 6.

As can be seen from FIGS. 1 to 6, the cobalt and nickel compounds of the present disclosure suffered rapid decrease in weight at a temperature range from 100° C. to 230° C. As for the compounds represented by the chemical formulas 7 and 8, temperatures $T_{1/2}$ where the weights of the samples reach halves (½) of their original weights were 180° C. and 199° C., respectively. Further, DSC graphs of the compounds represented by the chemical formulas 7 and 8 exhibit endothermic peaks at 272° C. and 239° C., respectively.

Experimental Example 2

Isothermal TGA

In order to evaluate thermal stability of cobalt and nickel compounds prepared in Examples 1, 5, 9, and 11, isothermal TGA was performed at temperatures of 80° C., 100° C., 120° C. and 150° C. At this time, about 5 mg of each of the samples was put into a sample vessel and heated at a heating rate of 10° C./min. Then, after reaching each temperature, measurement was performed for about 2 hours. Measurement results are provided in FIGS. 7 to 10.

As can be seen from FIGS. 7 to 10, all of the cobalt and nickel compounds synthesized in the present disclosure were found to volatilize at a temperature equal to or less than about 150° C. without being deformed or thermally decomposed.

Experimental Example 3

Deposition of Cobalt and Nickel Thin Films by Chemical Vapor Deposition

Evaluation of thin films formed by chemical vapor deposition (CVD) was performed by using the liquid cobalt compound of the chemical formula 7 prepared in Example 1 and the liquid nickel compound of the chemical formula 11 prepared in Example 5 as precursors. A Si (001) plane wafer was used as a substrate. A Pyrex tube having an inner diameter of 5 cm and a length of 40 cm was used as deposition equipment, and one end of this Pyrex tube was stuffed with the cobalt and nickel compounds. During deposition, temperatures of both precursors were maintained constant at 90° C., and a reactor was connected to a vacuum pump ($10^{-2}$ torr) maintained in a low vacuum state ranging from 120 mtorr to 300 mtorr. The substrate was maintained at a temperature of 250° C.

Figure 11:
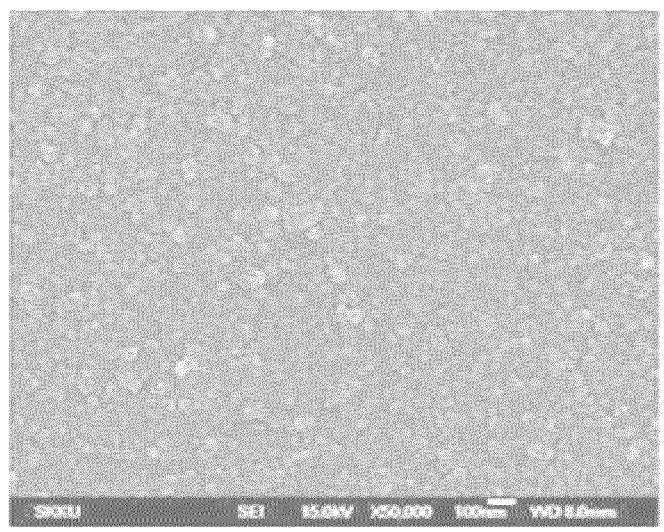
FIG. 11 is a SEM (Scanning Electron Microscope) image of a cobalt metal thin film formed in Experimental Example 3 of the present disclosure.
Figure 11:
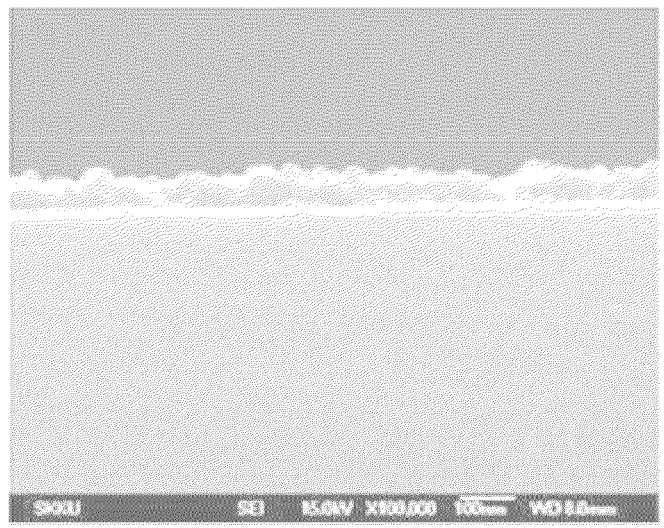
Figure 12:
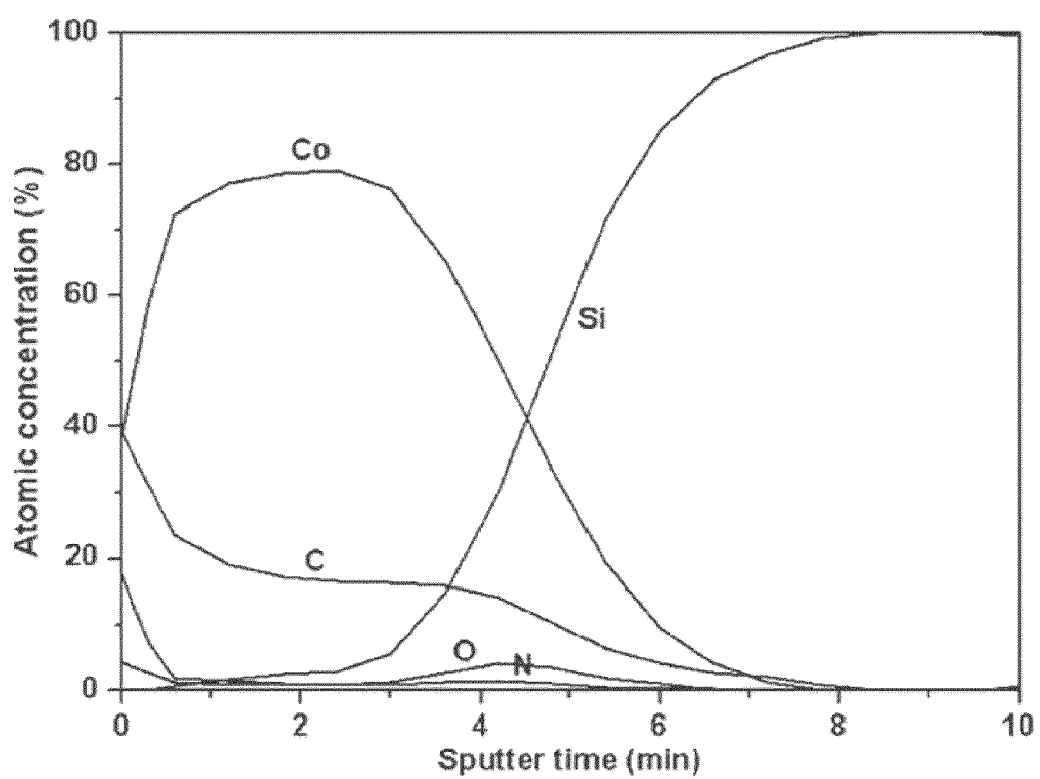
FIG. 12 shows an Auger analysis result of the cobalt metal thin film formed in Experimental Example 3 of the present disclosure.
Figure 13:
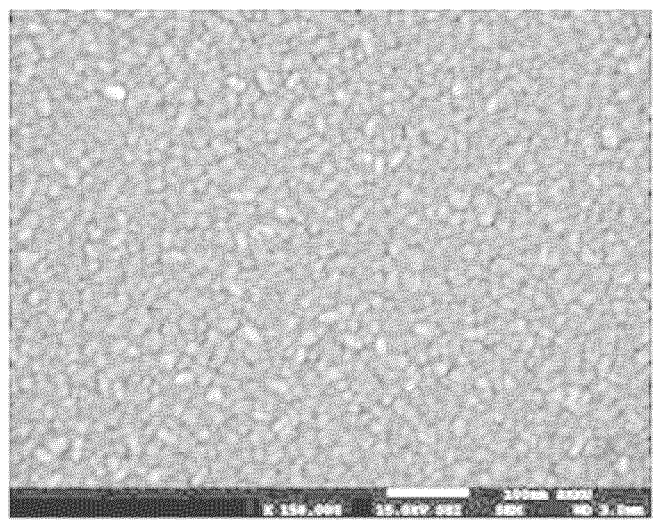
FIG. 13 is a SEM image of a nickel metal thin film formed in Experimental Example 3 of the present disclosure.
Figure 13:
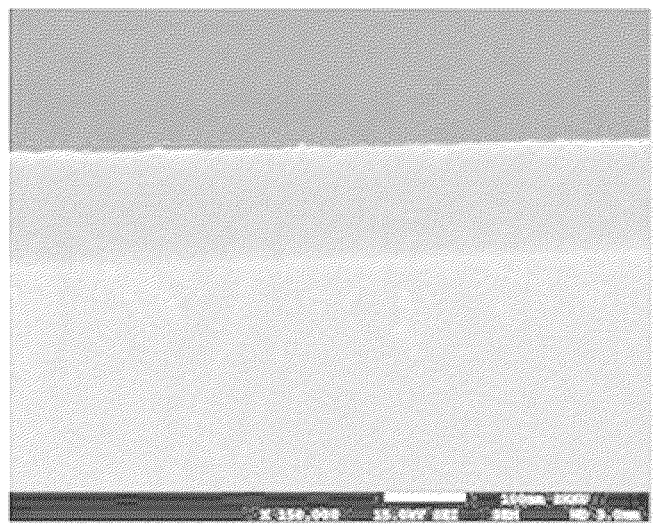
Figure 14:
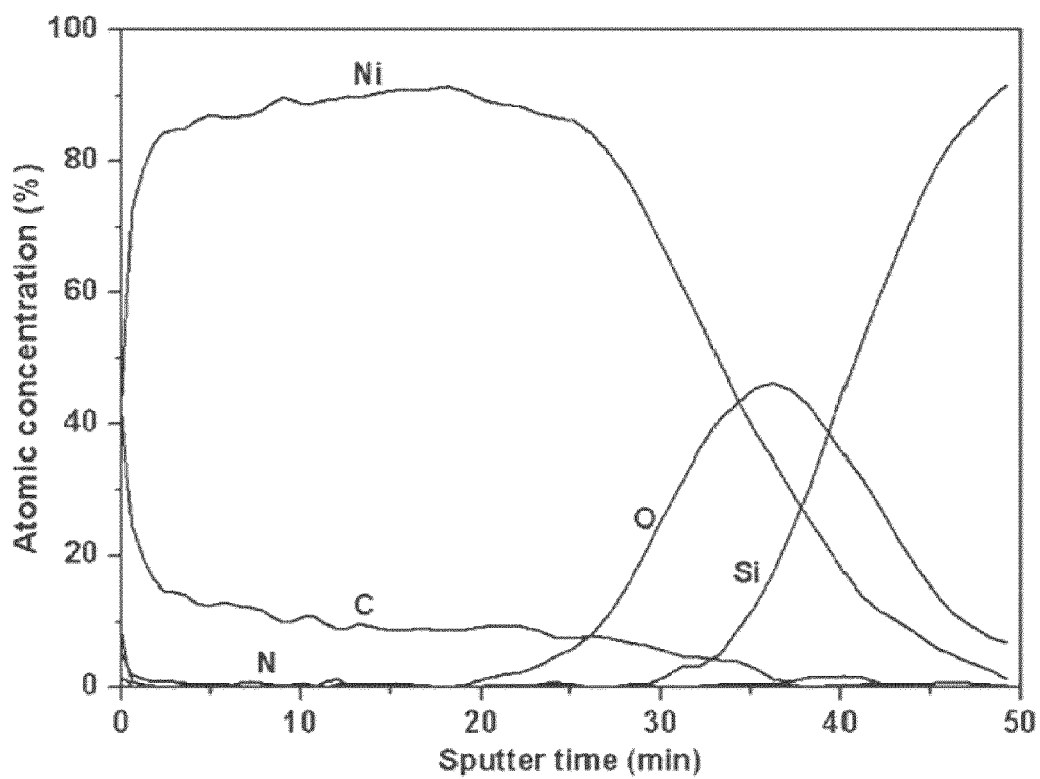
FIG. 14 shows an Auger analysis result of the nickel metal thin film formed in Experimental Example 3 of the present disclosure.

Images of surfaces and cross sections of cobalt and nickel thin films formed at the temperature of 250° C. for 1 hour were observed by using a scanning electron microscope. The images are shown in FIGS. 11 and 13. Further, the cobalt thin film deposited by using the cobalt compound was analyzed by using an Auger electron spectrometer, and the contents of carbon (C), nitrogen (N), oxygen (O) and cobalt (Co) are shown in FIG. 12. Likewise, the nickel thin film deposited by using the nickel compound was also analyzed and the contents of carbon, nitrogen, oxygen and nickel (Ni) are specified in FIG. 14.

As can be seen from the above analysis, a cobalt metal film containing about 20% of carbon was found to be formed on a surface of the substrate by chemical deposition in which the cobalt compound of the chemical formula 7 was used without using any reactant gas. Further, it was also found out that a nickel metal film containing about 10% of carbon was formed on the surface of the substrate by chemical deposition in which the nickel compound of the chemical formula 11 was used without using any reactant gas.

Experimental Example 4

Deposition of Cobalt Oxide Thin Film by Chemical Vapor Deposition

Among the metal diazadiene-based compounds in accordance with the present disclosure, by using the liquid cobalt compound of the chemical formula 7 prepared in Example 1 as a precursor and an oxygen ($O_2$) gas as a reactant gas, a cobalt oxide film was formed by chemical vapor deposition. A Si (001) plane wafer was used as a substrate.

After locating the silicon substrate within a chamber, an internal pressure of the chamber was adjusted to 1.5 Torr. The substrate was heated to a temperature of 300° C. The precursor was accommodated in a bubbler vessel made of stainless steel. Then, while heating the vessel at a temperature of 90° C., bubbling of the vessel was performed by using an argon gas with a flow rate of 200 sccm as a carrier gas for the precursor to thereby vaporize the precursor. At this time, an oxygen gas was introduced into the chamber at a flux of 20 sccm as a reactant gas that would react with the cobalt precursor in the chamber.

Figure 15:
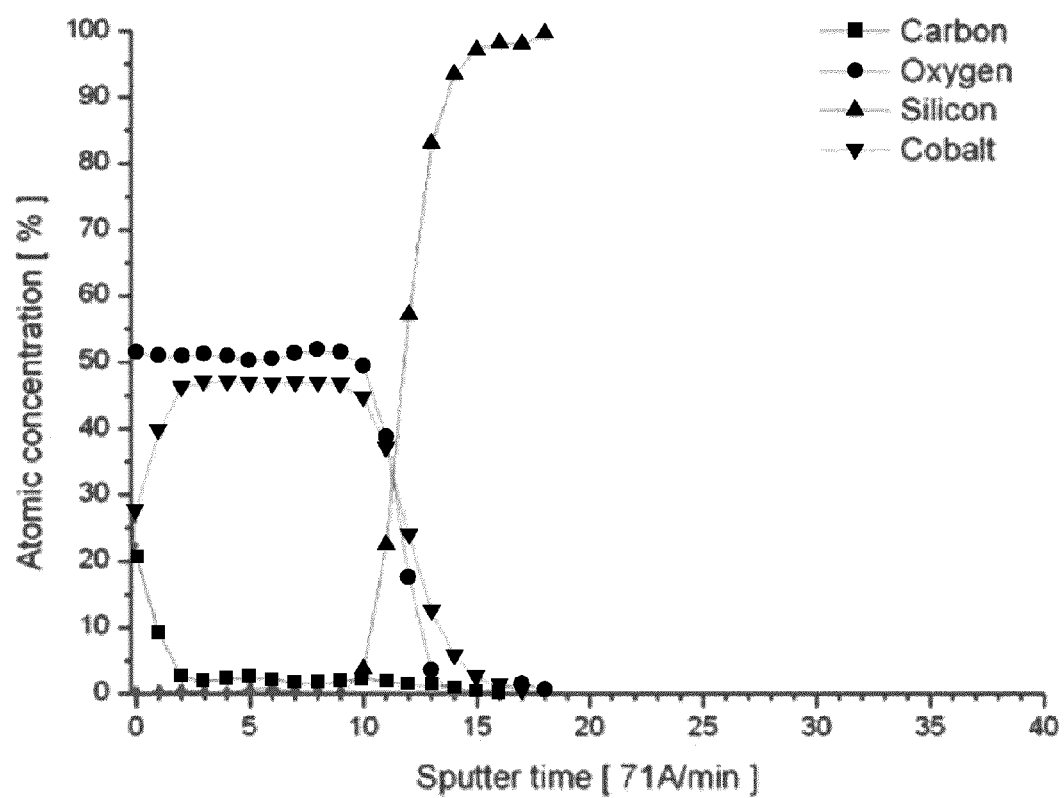
FIG. 15 provides an Auger analysis result of a cobalt oxide thin film formed in Experimental Example 4 of the present disclosure.

The contents of carbon, oxygen and cobalt in a thin film deposited at the temperature of 300° C. for 30 minutes were measured by using an Auger electron spectrometer, and the measurement result is provided in FIG. 15. From the graph of FIG. 15, it was proved that a cobalt oxide thin film having a composition close to CoO was formed.

The above description of the present disclosure is provided for the purpose of illustration, and it would be understood by those skilled in the art that various changes and modifications may be made without changing technical conception and essential features of the present disclosure. Thus, it is clear that the above-described illustrative embodiments are illustrative in all aspects and do not limit the present disclosure. For example, each component described to be of a single type can be implemented in a distributed manner. Likewise, components described to be distributed can be implemented in a combined manner.

The scope of the inventive concept is defined by the following claims and their equivalents rather than by the detailed description of the illustrative embodiments. It shall be understood that all modifications and embodiments conceived from the meaning and scope of the claims and their equivalents are included in the scope of the inventive concept.

What is claimed is:

1. A diazadiene-based metal compound represented by any one of the following chemical formulas 1 to 4:

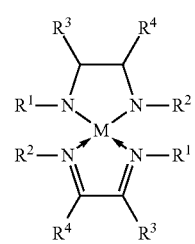

<Chemical formula 1>

<Chemical formula 2>

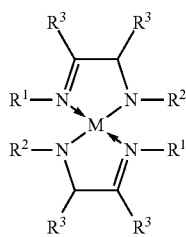

<Chemical formula 3>

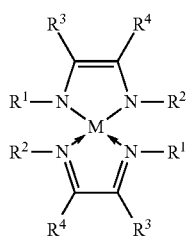

<Chemical formula 4>

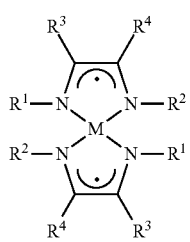

wherein in the chemical formulas 1 to 4,

M denotes Ni, Mn or Co, and $R^1$ and $R^2$ are iso-propyl groups and $R^3$ and $R^4$ are hydrogen, and wherein the diazadiene-based metal compound is liquid.

2. A diazadiene-based metal compound represented by any one of the following chemical formulas 1 to 4:

<Chemical formula 1>

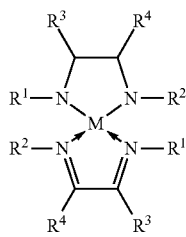

<Chemical formula 2>

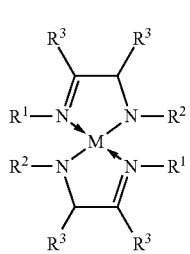

<Chemical formula 3>

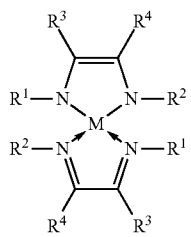

<Chemical formula 4>

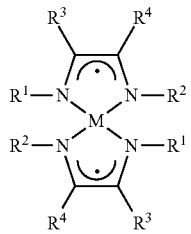

wherein in the chemical formulas 1 to 4,

M denotes Ni, Co or Mn, and wherein $R^1$ and $R^2$ are iso-propyl groups and $R^3$ and $R^4$ are hydrogen.

3. The diazadiene-based metal compound of claim 2, wherein the diazadiene-based metal compound is represented by the chemical formula 3, in which $R^1$ and $R^2$ are iso-propyl groups and $R^3$ and $R^4$ are hydrogen.

4. The diazadiene-based metal compound of claim 2, wherein the diazadiene-based metal compound is represented by the chemical formula 4 in which $R^1$ and $R^2$ are iso-propyl groups and $R^3$ and $R^4$ are hydrogen.

5. A thin film forming method, comprising:

depositing a diazadiene-based metal compound used as a source material on a substrate by chemical vapor deposition or atomic layer deposition to form a metal thin film containing nickel, cobalt or manganese, wherein the diazadiene-based metal compound is represented by any one of the following chemical formulas 1 to 4:

<Chemical formula 1>

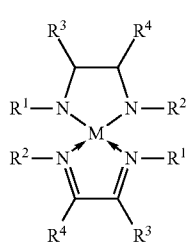

<Chemical formula 2>

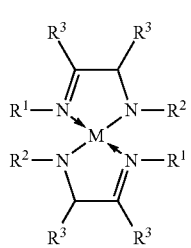

-continued

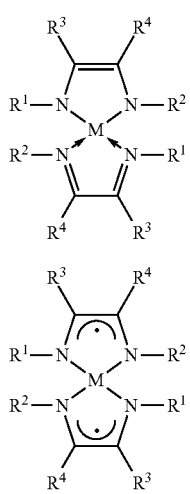

<Chemical formula 3>

<Chemical formula 4> wherein in the chemical formulas 1 to 4,
M denotes Ni, Co or Mn, and
wherein $R^1$ and $R^2$ are iso-propyl groups and $R^3$ and $R^4$ are hydrogen, and
wherein the diazadiene-based metal compound is a liquid.

6. The thin film forming method of claim 5, wherein the diazadiene-based metal compound is in a gaseous state.

7. The thin film forming method of claim 5, wherein a deposition temperature ranges from 50° C. to 700° C. when the diazadiene-based metal compound is deposited.

8. The thin film forming method of claim 6, wherein the diazadiene-based metal compound in the gaseous state is delivered onto the substrate by a method selected from the group consisting of a bubbling method, a vapor phase mass flow controller (MFC) method, a direct liquid injection (DLI) method, and a liquid delivery system (LDS) for delivering the compound while dissolving the compound in an organic solvent.

9. The thin film forming method of claim 5, further comprising:
using a reactant gas selected from the group consisting of water vapor, oxygen, ozone, hydrogen, ammonia, alcohols, aldehydes, carboxylic acids, silanes, and their combinations, when the diazadiene-based metal compound as a source material is used.

10. The diazadiene-based metal compound of claim 2, wherein the diazadiene-based metal compound is represented by the chemical formula 2, in which $R^1$ and $R^2$ are iso-propyl groups and $R^3$ is hydrogen.

* * * * *